US008688466B2

(12) United States Patent
Kharraz Tavakol et al.

(10) Patent No.: US 8,688,466 B2
(45) Date of Patent: *Apr. 1, 2014

(54) DATA SYNCHRONIZATION FOR BOOKING OF HEALTHCARE APPOINTMENTS ACROSS PRACTICE GROUPS

(75) Inventors: Oliver D. Kharraz Tavakol, New York, NY (US); Cyrus E. Massoumi, New York, NY (US)

(73) Assignee: ZocDoc, Inc., New York, NY (US)

( * ) Notice: Subject to any disclaimer, the term of this patent is extended or adjusted under 35 U.S.C. 154(b) by 1272 days.

This patent is subject to a terminal disclaimer.

(21) Appl. No.: 12/210,765

(22) Filed: Sep. 15, 2008

(65) Prior Publication Data

US 2010/0070297 A1    Mar. 18, 2010

(51) Int. Cl.
 *G06Q 50/00*  (2012.01)
 *G06Q 50/22*  (2012.01)

(52) U.S. Cl.
 CPC ..................................... *G06Q 50/22* (2013.01)
 USPC ............................................................ 705/2

(58) Field of Classification Search
 CPC .......................................... G06Q 50/22–50/24
 USPC ....................................................... 705/2–3
 See application file for complete search history.

(56) References Cited

U.S. PATENT DOCUMENTS

| | | | |
|---|---|---|---|
| 6,067,523 A * | 5/2000 | Bair et al. ......................... | 705/3 |
| 6,345,260 B1 | 2/2002 | Cummings | |
| 6,389,454 B1 | 5/2002 | Ralston et al. | |
| 6,477,503 B1 | 11/2002 | Mankes | |
| 6,757,898 B1 | 6/2004 | Ilsen et al. | |
| 6,839,680 B1 | 1/2005 | Liu et al. | |
| 6,876,973 B1 * | 4/2005 | Visconti ............................ | 705/5 |
| 7,069,228 B1 | 6/2006 | Rose et al. | |
| 7,174,303 B2 | 2/2007 | Glazer et al. | |
| 7,212,985 B2 | 5/2007 | Sciuk | |
| 7,596,513 B2 * | 9/2009 | Fargo ......................... | 705/26.62 |
| 7,752,060 B2 * | 7/2010 | Hicks et al. ...................... | 705/3 |
| 7,797,170 B2 | 9/2010 | Bodin | |
| 7,904,334 B2 * | 3/2011 | Chen et al. ................... | 705/14.4 |
| 2002/0116220 A1 | 8/2002 | Glazier | |
| 2003/0061087 A1 * | 3/2003 | Srimuang ......................... | 705/8 |
| 2004/0010423 A1 | 1/2004 | Sameh | |
| 2004/0158486 A1 | 8/2004 | Nudd et al. | |

(Continued)

FOREIGN PATENT DOCUMENTS

WO    WO02/056131 A2    7/2002

OTHER PUBLICATIONS

Anonymous. "ZocDoc Launches at TechCrunch40 Conference", Business Wire. New York: Sep 18, 2007.*

(Continued)

*Primary Examiner* — Dilek B Cobanoglu
*Assistant Examiner* — Robert Sorey
(74) *Attorney, Agent, or Firm* — Novak Druce Connolly Bove + Quigg LLP

(57) ABSTRACT

Systems and methods for aggregating available healthcare appointment times across multiple unaffiliated practitioner groups, including search and display algorithms. A centralized marketplace is provided for real time booking of healthcare appointments which does not require the patient to have a preexisting relationship with the practitioner. The aggregated booking system enhances the number of available near term and conveniently located appointment options while the search and display algorithms reduce the complexity of the patient and practitioner information required to maintain accurate and synchronized database booking records.

19 Claims, 34 Drawing Sheets

(56) References Cited

U.S. PATENT DOCUMENTS

| | | | |
|---|---|---|---|
| 2004/0198331 | A1 | 10/2004 | Coward et al. |
| 2004/0199404 | A1 | 10/2004 | Ripperger et al. |
| 2004/0199412 | A1 | 10/2004 | McCauley |
| 2004/0236601 | A1 | 11/2004 | Summers et al. |
| 2005/0165627 | A1 | 7/2005 | Fotsch et al. |
| 2005/0172325 | A1* | 8/2005 | Henry et al. .................. 725/116 |
| 2006/0129444 | A1 | 6/2006 | Baeza et al. |
| 2007/0106752 | A1 | 5/2007 | Moore |
| 2007/0112610 | A1* | 5/2007 | Johnson et al. .................... 705/8 |
| 2007/0203761 | A1* | 8/2007 | Keen ................................ 705/5 |
| 2007/0226010 | A1 | 9/2007 | Larsen |
| 2008/0109262 | A1* | 5/2008 | Dvorak et al. .................... 705/3 |
| 2008/0109361 | A1 | 5/2008 | Urali et al. |
| 2008/0249830 | A1* | 10/2008 | Gilman et al. .................... 705/9 |
| 2009/0076855 | A1 | 3/2009 | McCord |
| 2009/0089085 | A1* | 4/2009 | Schoenberg ...................... 705/2 |
| 2009/0119126 | A1* | 5/2009 | Johnson et al. .................... 705/2 |
| 2009/0164252 | A1* | 6/2009 | Morris et al. ..................... 705/3 |
| 2010/0017222 | A1 | 1/2010 | Yeluri et al. |
| 2010/0042461 | A1* | 2/2010 | Carpenter et al. ................ 705/9 |
| 2010/0180211 | A1* | 7/2010 | Boyd ............................ 715/751 |
| 2011/0009707 | A1 | 1/2011 | Kaundinya et al. |
| 2011/0059727 | A1* | 3/2011 | Lisboa ....................... 455/414.1 |
| 2012/0136671 | A1* | 5/2012 | Alt et al. ........................... 705/2 |
| 2012/0203579 | A1* | 8/2012 | Glasson et al. ................... 705/5 |

OTHER PUBLICATIONS

Colliver, Victoria. "For these startups, patients are a virtue", San Francisco Chronicle. San Francisco, Calif.: Oct 1, 2007. p. C.1.*
ZocDoc. "ZocDoc BETA Dentist and Doctor Appointments", a Feb. 20, 2008 entry of www.zocdoc.com accessed at www.archive.org on Jun. 24, 2011.*
Dec. 22, 2010 Office Action in U.S. Appl. No. 12/210,690.
Mar. 10, 2011 Office Action in U.S. Appl. No. 12/210,716.
www.google.com/patents search result.
May 20, 2011 Office Action in copending and commonly owned U.S. Appl. No. 12/210,716.
Jun. 6, 2011 International Search Report and Written Opinion in copending and commonly owned PCT/US2011/027207.
Oct. 1, 2010 Office Action in U.S. Appl. No. 12/210,716.
OpenTable.com (http://www.opentable.com/) provides a website (consumer portal) that allows users to book tables at different restaurants. However, to applicant's knowledge, the offered tables are reserved (given up) by the individual restaurants for OpenTable.com, and thus the reserved tables are handled separately from any other available tables the restaurant may have. To applicant's knowledge, the system also does not accommodate different types of bookings, with corresponding durations, of the table allocation, (e.g. it does not allow to book just for drinks, or desserts, or a full dinner.)
NexSched (http://www.nexsched.com/index.html) provides a data synchronization product for online booking of medical appointments. However, to applicant's knowledge, this product allows booking only from one medical practice group. Also, to applicant's knowledge, the product does not cache the availability data, rather it requests information each time a patient starts a query (similar to the Saber travel service). To applicant's knowledge, the product does check for changes before it writes a booking back to the practice database to provide data synchronization.
*Xoova*—This company previously had a website (consumer portal) for requesting medical appointments from multiple practice groups. To applicant's knowledge the Xoova website launched sometime in Nov./Dec. 2007 and subsequently folded. To applicant's knowledge, the Xoova platform did not offer standardized appointment types, nor did it offer real/time appointment bookings, because availability was not saved on the Xoova servers. Rather, when the user requested an appointment, the request was transmitted to the provider (group), manually reviewed and responded to.
Patient Interface Mockup (May 2007).
The Record, Sep. 10, 2008, "Helping Choose the Right Doctor for You, Vitals.com CEO found inspiration in the OR", 2 pages.
The Deal.com, Oct. 13, 2008 "Vitals.com locates $4M", 2 pages.
GObookings Systems Pty Ltd attorney letter dated Jul. 24, 2013 (received by applicant's attorney Jul. 29, 2013).

* cited by examiner

Fig.16

| id | practice id | client id | client location id | procedure id | start time | end time | status | booking id | duration |
|---|---|---|---|---|---|---|---|---|---|
| x | 1221 | 501 | 200 | NULL | 9/9/2008 11:30 | 9/9/2008 12:15 | NULL | NULL | 45 |
| x | 1221 | 501 | 200 | NULL | 9/9/2008 9:15 | 9/9/2008 10:45 | NULL | NULL | 90 |
| x | 1221 | 501 | 200 | NULL | 9/5/2008 10:00 | 9/5/2008 12:15 | NULL | NULL | 135 |
| x | 1039 | 75 | 22 | NULL | 9/5/2008 14:45 | 9/5/2008 15:30 | NULL | NULL | 45 |
| x | 1221 | 496 | 200 | NULL | 9/5/2008 10:00 | 9/5/2008 12:15 | NULL | NULL | 135 |
| x | 1042 | 79 | 25 | NULL | 8/29/2008 6:00 | 8/29/2008 6:45 | NULL | NULL | 45 |
| x | 1134 | 307 | 98 | NULL | 9/8/2008 12:00 | 9/8/2008 12:30 | NULL | NULL | 30 |
| x | 1134 | 307 | 98 | NULL | 9/3/2008 11:45 | 9/3/2008 13:00 | NULL | NULL | 75 |
| x | 1134 | 307 | 98 | NULL | 9/10/2008 18:00 | 9/10/2008 19:00 | NULL | NULL | 60 |
| x | 1134 | 307 | 98 | NULL | 9/10/2008 14:30 | 9/10/2008 16:00 | NULL | NULL | 90 |
| x | 1134 | 307 | 98 | NULL | 9/3/2008 15:45 | 9/3/2008 16:00 | NULL | NULL | 15 |
| x | 1134 | 307 | 98 | NULL | 9/17/2008 18:45 | 9/17/2008 19:00 | NULL | NULL | 15 |
| x | 1134 | 307 | 98 | NULL | 9/17/2008 11:30 | 9/17/2008 17:30 | NULL | NULL | 360 |
| x | 1134 | 307 | 98 | NULL | 9/4/2008 15:00 | 9/4/2008 15:30 | NULL | NULL | 30 |
| x | 1134 | 307 | 98 | NULL | 9/4/2008 17:45 | 9/4/2008 19:00 | NULL | NULL | 75 |
| x | 1221 | 496 | 200 | NULL | 9/5/2008 9:15 | 9/5/2008 10:00 | 2 | 2541 | 45 |
| x | 1042 | 79 | 125 | NULL | 9/4/2008 10:15 | 9/4/2008 11:00 | 2 | 2540 | 45 |
| x | 1211 | 465 | 193 | NULL | 8/28/2008 20:15 | 8/28/2008 21:00 | 2 | 2531 | 45 |
| x | 1108 | 258 | 77 | NULL | 8/29/2008 14:35 | 8/29/2008 14:55 | 2 | 2536 | 20 |

Fig.19B

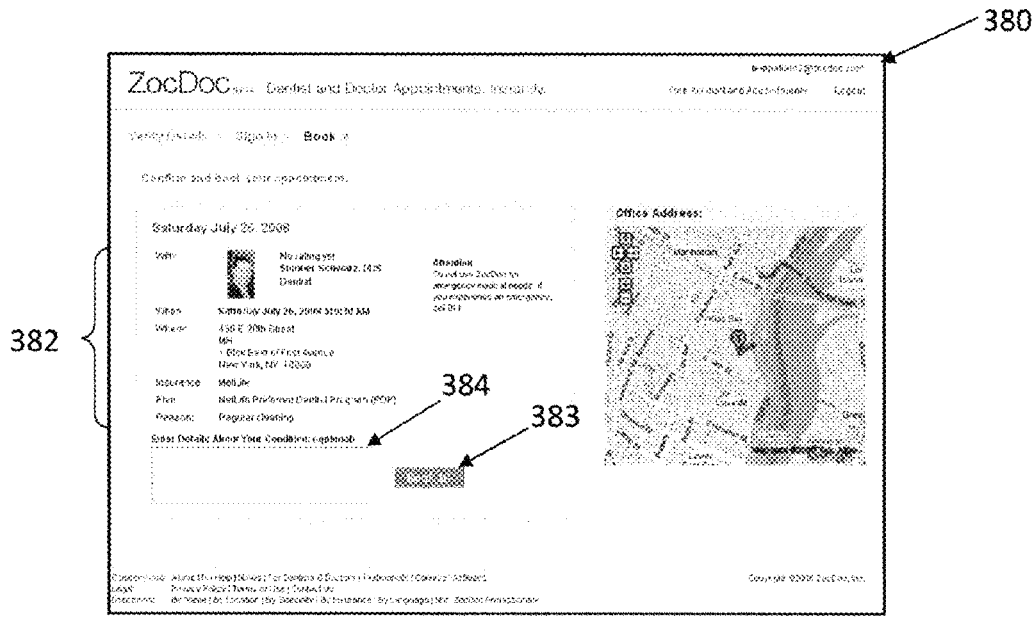

Fig.28A

From: ZocDoc   service@zocdoc.com
Date: Thu, Sep 11, 2008 at 12:18 AM
Subject: Your ZocDoc appointment on Thursday September 11, 2008 at 3:45PM
To: zocdoc@doddrell.com Thank you for booking with ZocDoc! Our system has reserved this appointment with James Smith, AASN, ASN for you.

Here's what happens next:
1. The office of James Smith, AANS, ASN will confirm your appointment through our system.
2. We will send you an automatic confirmation e-mail once they do.
3. You see your doctor at the time you chose!

Your appointment details appear below.

Patient: Trevor Doddrell

With: James Smith, AASN, ASN

When: Thursday September 11, 2008 at 3:45PM

Where: 123 45st
2nd Floor
2nd Ave
New York, NY, 10003
1234567890

Reason: Regular Cleaning

Insurance: My Dr. already has my details

Our doctors guarantee availability for times booked on ZocDoc. I the doctor didn't see you at the exact time you booked; we want to know about it. Please let us know here:
http://www.zcdoc.com/patients/reschudledfeedback.aspx?id=aced46cf-3810-4634-a5f7-b865ebcabfe3

If you need to change or cancel your appointment, please do so at
http://www.zocdoc.com/patients/myappointments.aspx

Fig.28B

From: ZocDoc   service@zocdoc.com
Date: Thu, Sep 11, 2008 at 12:29 AM
Subject: Your ZocDoc appointment has been confirmed
To: zocdoc@doddrell.com The office of James Smith, AASN, ASN was notified of your appointment booked on ZocDoc, and
It has been confirmed by them. Details of the confirmed appointment are as follows.

Patient:   Trevor Doddrell

With:   James Smith, AASN, ASN

When:   Thursday September 11, 2008 at 12:29 AM

Where:   123 45st
        2$^{nd}$ Floor
        2$^{nd}$ Ave
        New York, NY, 10003
        1234567890

Reason:   Regular Cleaning

Insurance: I'm paying myself

If you need to change or cancel your appointment, please do so at
http://www.zocdoc.com/patients/myappointments.aspx Please note that you may also be contacted by the office of James Smith, AASN, ASN.

Fig.29

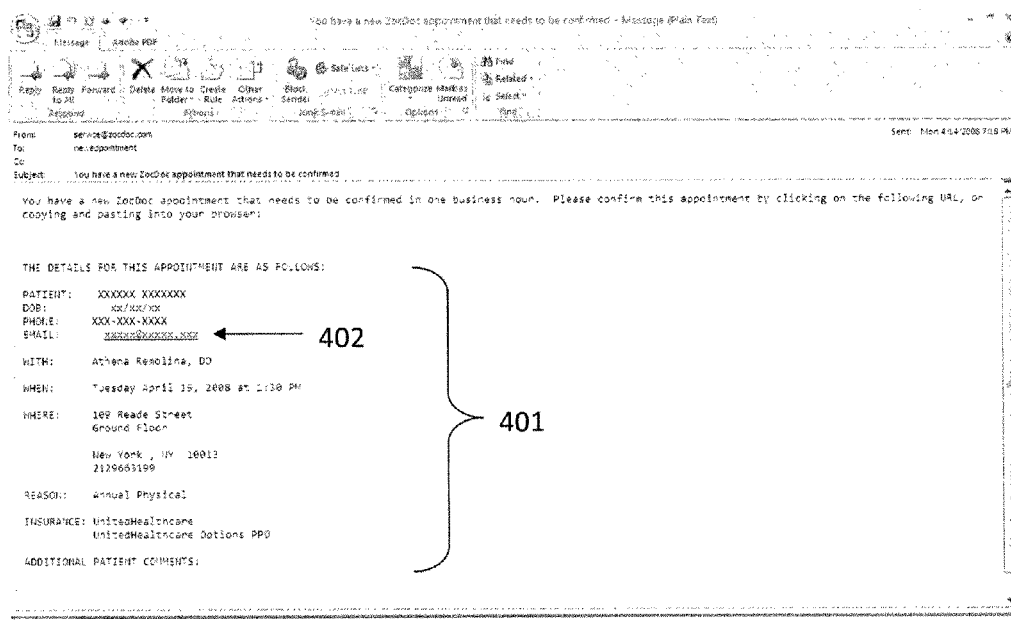

Fig.30

DATA SYNCHRONIZATION FOR BOOKING OF HEALTHCARE APPOINTMENTS ACROSS PRACTICE GROUPS

FIELD OF THE INVENTION

The present invention relates to systems and methods for aggregating available appointment times across multiple practitioner groups, including search and display algorithms.

BACKGROUND

The booking of healthcare appointments has long been handled via telephone and within a specific group of affiliated healthcare practitioners. The reasons for this are many, including the need to match a great variety of patient needs with the available physician resources, the desire of physicians to maintain control over their working hours and practice, which are essentially dictated by their appointment schedules, the affiliations among insurance companies, plans, fee schedules and accepted procedures, and the patient's desire and comfort level with selecting their own physician.

As a result, prior attempts to automate this process have generally been unsuccessful. The human receptionist in the doctor's office continues to be central focal point for booking an appointment from the viewpoint of both the physician and the patients. The receptionist has the required knowledge base to satisfy both the needs and comfort levels of the physicians in the practice group and their patients. However, telephone based booking of healthcare appointments is time consuming and very often inconvenient for the patient. For example, call in times are limited to the receptionist's working hours and the volume of calls being handled by the receptionist. Still further, the above scenario assumes the patient has a preexisting relationship with a physician, and that physician has a convenient or acceptable appointment time for the necessary procedure. Finding a new physician is even more time consuming for the patient, involving researching potential local practice groups, physician backgrounds, and calls to see whether the physician is accepting new patients. Thus, while there is much room for improvement, there has been very little success in implementing an alternative process for booking healthcare appointments.

SUMMARY OF THE INVENTION

Systems and methods are provided for aggregating available healthcare appointment times across multiple unaffiliated practitioner groups, including search and display algorithms. A centralized marketplace is provided for real time booking of healthcare appointments which does not require the patient to have a preexisting relationship with the practitioner. The aggregated booking system enhances the number of available near term and conveniently located appointment options while the search and display algorithms reduce the complexity of the patient and practitioner information required to maintain accurate and synchronized database booking records.

In accordance with one embodiment of the invention, a method is provided comprising:

an aggregator of healthcare appointments maintains a central database of available healthcare appointments for a plurality of healthcare practice groups, and the aggregator provides a website for online booking of available healthcare appointments from the practice groups;

each practice group has its own database of its own available healthcare appointments; and appointments are offered to patients from both databases concurrently by the aggregator and the various practice groups;

the practice groups and aggregator communicate via a computer network and program code which automatically pulls available appointment times from the practice group databases for the aggregator database; and the aggregator sends the practice groups notices to check for and confirm availability of appointments.

According to one embodiment, the method includes:
determining based on the central database whether a practice group has less than a predetermined number of available appointments, and if true, sending the practice group a notice.

According to one embodiment, the method includes:
determining based on the central database whether a practice group will have no available appointments after a defined time period, and if true, sending the practice group a notice.

According to one embodiment, the method includes:
determining from the central database whether a practice group has no available appointment times, and if true, sending the practice group a notice.

According to one embodiment, the method includes:
determining from the central database whether a practice group has less than a predetermined number of available appointment times, and if true, sending the practice group a message that other practice groups are receiving appointments.

According to one embodiment, the method includes:
prior to a holiday, sending the practice groups a request to verify available appointments in the central database which fall on the holiday.

According to one embodiment, the method includes:
the aggregator communicating in predefined intervals with the practice groups to obtain changed appointment data from the practice group databases.

According to one embodiment, the method includes:
providing an application on a practice group server remote from an aggregator server, for communicating changes of appointment data between the central database and the practice group database.

In accordance with another embodiment of the invention, a method is provided comprising:

an aggregator of healthcare appointments maintains a central database of available healthcare appointments for a plurality of healthcare practice groups, and the aggregator provides a website for online booking of available healthcare appointments from the practice groups;

each practice group has its own database of its own available healthcare appointments;

appointments are offered to patients from both databases concurrently by the aggregator and the various practice groups; and the practice groups send the aggregator available appointment times for an associated practitioner in time blocks, wherein a time block includes multiple contiguous available appointment times.

According to one embodiment, the method includes:
each practice group specifying a minimum procedure time for a practitioner;

the aggregator determining a plurality of available starting time slots from the time block based upon the specified procedure time.

According to one embodiment, the method includes:
the aggregator offering via its website the starting time slots for an associated practitioner.

According to one embodiment, the method includes:
the aggregator stores available appointment times as the time blocks and determines the time slots after receiving an online request for an appointment via the website.

According to one embodiment, the method includes:
the practice group specifying one or more allowed procedure types to be booked in an available appointment time.

In accordance with another embodiment of the invention, a method is provided comprising:
an aggregator of healthcare appointments maintains a central database of available healthcare appointments for a plurality of healthcare practice groups, and the aggregator provides a website for online booking of available healthcare appointments from the practice groups;
each practice group has its own database of its own available healthcare appointments;
appointments are offered to patients from both databases concurrently by the aggregator and the various practice groups; and
when a patient books an online appointment from the aggregator's website, the aggregator notifies the practice group to confirm the booked appointment within a defined time period.

According to one embodiment, the method includes:
the aggregator imposes a penalty on the practice group if it fails to confirm the appointment within the defined time period.

According to one embodiment, the method includes:
the practice group and aggregator communicate via a computer network and program code which automatically pulls available appointment time from the practice group database.

According to one embodiment, the method includes:
the program code automatically alerts the practice group of a booked appointment which requires confirmation.

According to one embodiment, the method includes:
the program code automatically blocks requests to book appointments which are less than a threshold time defined to provide the practice group sufficient time to confirm the booked appointment.

In accordance with another embodiment of the invention, a method is provided comprising:
an aggregator of healthcare appointments maintains a central database of available healthcare appointments for a plurality of healthcare practice groups, and the aggregator provides a website for online booking of available healthcare appointments from the practice groups;
each practice group has its own database of its own available healthcare appointments;
appointments are offered to patients from both databases concurrently by the aggregator and the various practice groups; and
the aggregator's website offers defined practitioner specialties and defined procedure types from which a patient selects to book an appointment; and
the practice group specifies a procedure time for an associated practitioner and procedure type.

According to one embodiment, the method includes:
the aggregator determines and offers on its website available starting time slots for an associated practitioner and procedure based on a minimum procedure time of the practitioner.

According to one embodiment, the method includes:
the aggregator's website offers defined insurance carriers and plans from which a patient selects to book an appointment; and
the practice group specifies insurance carriers and plans for each of its practitioners.

BRIEF DESCRIPTION OF THE DRAWINGS

FIG. 16 is a CSR display screen showing a customer service representative the details of appointment bookings for each of a plurality of clients;

FIG. 19b is an exemplary group of database records;

FIG. 28a is an exemplary webpage enabling a patient to confirm and book an appointment;

FIG. 28b is an exemplary email sent to a patient after booking an appointment (prior to confirmation);

FIG. 29 is an exemplary email set to a patient that the appointment has been confirmed by the practitioner (client);

FIG. 30 is an exemplary email sent to a client requesting confirmation of a newly booked appointment;

DETAILED DESCRIPTION

Figure 1A:
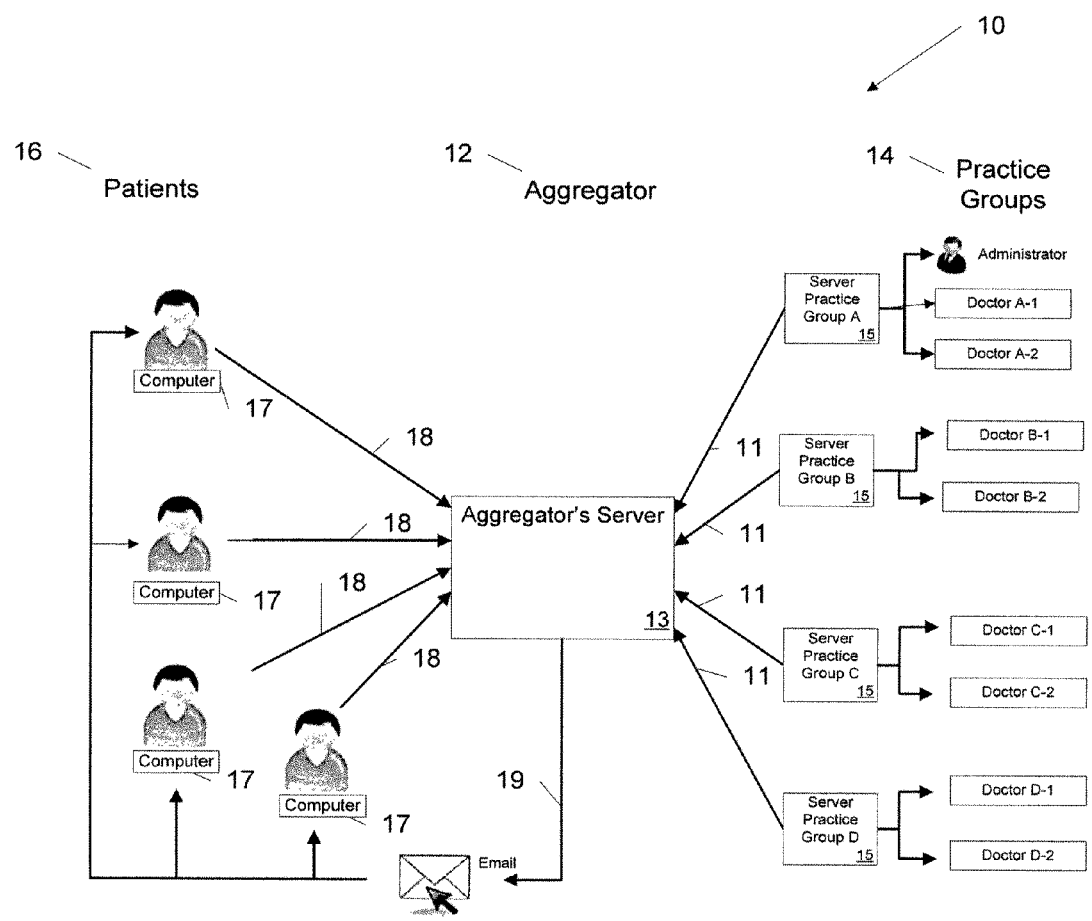
FIG. 1a shows an exemplary marketplace (community) enabling online booking of healthcare appointments across practitioner groups according to one embodiment of the invention.

In accordance with various embodiments of the present invention, a consumer portal for booking healthcare appointments across practitioner groups is provided. The consumer, a prospective patient, may or may not be an existing patient of the practice group with whom the appointment will be booked via the portal. The booking procedure is essentially immediate, enabling a patient to view a listing of available appointment times across various practitioner groups and then make an informed selection that satisfies the needs of this specific patient. The patient is provided with a wide range of available appointment times, much broader than would be available from any one practice group. Further, the patient is provided with options for selecting among the available appointment slots, based on a variety of factors including location, near availability of the appointment, insurance plans accepted, background of the practitioner (e.g. doctor or dentist), patient feedback, and others. Perhaps the ultimate convenience, the patient can book the appointment essentially immediately online through a web browser.

The various embodiments of the invention described herein also satisfy the needs and desires of the various practice groups. The practice group can offload much of the manpower required for booking appointments to another entity, but still maintain control of its own appointment schedule. Procedures are employed to ensure that the appointments being booked are viable appointments and will not likely result in a cancellation or no-show. The practitioners can more readily fill near term available slots in their appointment schedules which become available due to patient cancellations and re-bookings and/or due to changes in the practitioners' own schedules. There are essentially no changes required to be made in the doctor's or dentist's existing practice, rather the new booking procedure can be essentially transparent to, while being an enhancement of, their current practice procedures.

Various embodiment of the invention will now be described in the following subsections, and with reference to the drawings. First, a general overview of the new systems and methods is provided.

A booking platform is provided enabling various unaffiliated healthcare practitioner groups to provide, via a centralized aggregator, available healthcare appointments to prospective patients on the aggregator's website. The aggregator maintains a centralized database of available appointment times across the various practitioner groups, as well as information relevant to the practitioner and associated appointment times. The aggregator communicates with each of the practice groups and with a prospective patient while maintaining the database of available healthcare appointments and associated information for scheduling of appointments.

In accordance with one aspect of the invention, a consumer portal for healthcare appointments across practitioner groups is provided. The portal (website) combines cross practitioner booking functionality, patient reviews, patient reminders, patient insurance filtering, practitioner location information, and other practitioner profile information such as specialty, education and training background, languages spoken, etc.

In accordance with another aspect of the invention, a centralized database of available appointment information is maintained by the aggregator. The number and accuracy of the appointment times are enhanced by a variety of procedures. In one embodiment, a piece of software (client application) is installed on the practitioner's computer/server, which software automatically extracts from the practitioner's electronic practice management system (PMS), the available appointment times; this is done on a regular basis (e.g. intervals between 1-5 minutes) to insure that the aggregator has the most up to date availability. In addition, the client software may "ping" the aggregator's server periodically (e.g. every 15 minutes) to make sure that the aggregator knows if and when the client server is down (unavailable).

In another embodiment, synchronization between the aggregator and practice group is done via the aggregator's website. The practice group goes online (to the aggregator's website) and enters the available appointment times.

Because the aggregator has a centralized database of available appointment times, the aggregator can provide (via its website) essentially instantaneous booking of appointments by prospective patients. A patient logs onto the aggregator website and after opening an account with the aggregator, is allowed to book an appointment. The aggregator then notifies the practice group, e.g. via an email, letting them know that an appointment has been booked and providing a link within the email by which the practice group can elect to confirm the appointment. Alternatively, if the aggregator has installed an application on the client's (practice group's) computer, the client can be notified via a popup on their screen with a link to confirm the appointment. The popup may keep coming up until the appointment is confirmed.

If the practice group does not click on the link in their email or confirm the appointment by responding to the popup alerter, within a specified time, the aggregator may place a call to the practice office to confirm the appointment.

Various procedures are employed to insure the accuracy of the available appointment times. To give practice groups enough time to confirm appointments, when appointments are booked after business hours, patients may be prevented from booking early morning hour appointments on the next business day.

In accordance with another aspect of the invention, if a patient does not show up for an appointment, the aggregator may notify the patient that they are now blocked from booking future appointments, or if they again are a no-show in the future, they will be blocked from booking future appointments.

In accordance with another aspect of the invention, a practice group can enter their available time on the aggregator's system on the basis of a normal daily or weekly schedule, and then click a "recurring" button to have these times repeat for future days/weeks so they do not have to reenter those times. However, this can create a problem if one of those days in the future happens to be a holiday. To account for this, the aggregator sends the practice group automatic reminders before every public holiday asking them to confirm, if they are, in fact, open for business on this holiday. The aggregator may continue to send out this email every day before the holiday until the practitioner clicks on it letting the aggregator know whether or not they will be working on this holiday. This enables the aggregator to offer a recurring calendar function yet avoid problems with unintended bookings on holidays.

In another aspect, the aggregator sends reminder emails to practice groups if they are running out of available appointment times, notifying them that they should add additional appointment times. The aggregator may also inform the practice group how many appointments doctors have received in their area, since they last had available times in the system, as an incentive to add further available appointment times.

In accordance with another aspect of the invention, practitioners are allowed to designate the amount of time the individual practitioner needs for a given procedure. The aggregator fixes the available procedure types, but the practitioner can designate for each type of procedure whether it performs the procedure and what is the minimum time required to perform the procedure. Still further, the practitioner can indicate whether additional resources are required by the procedure, such as a hygienist or physician assistant or a particular piece of equipment. This enables the practice group to keep track of all resources—both human and non-human (e.g. equipment, rooms) needed for a scheduled appointment.

In a further aspect of the invention, before a patient can book an appointment, the aggregator requires the patient to submit his phone number. This phone number can serve multiple purposes. In one embodiment the aggregator can use the phone number to make sure that there is a unique phone number associated with each patient account, wherein a patient must have an account with the aggregator before he/she can book an appointment. Taking steps to ensure that one actual person has only one account can prevent abuse of the system, for example, where a person may try to disrupt the system by booking multiple appointments. Also, by linking appointments to unique patient accounts, the aggregator can track and limit the number of appointments booked by one patient. Further the aggregator can send the patient a code, e.g. via a text message or a phone call, and require the patient to enter that code on the aggregator's website before the patient is authorized to book an appointment. This also prevents appointment spam, while insuring that the aggregator, and the practitioner, have a correct phone number for the patient.

In accordance with another aspect of the invention, the aggregator employs a location verification procedure, again to deter appointment spam (bogus appointments). The geographic location of the patient is determined from the patient's IP address and compared to the geographic location of the selected appointment/practitioner. Far distances are flagged as this may indicate a fake appointment. The aggregator can then telephone the patient to verify the credibility of the appointment.

In accordance with another aspect of the invention, the aggregator implements various methods to detect abuse of the service by patients. Examples are patients who book appointments and do not show up or book appointments and repeatedly cancel at the last minute. Once the aggregator has detected abuse, the aggregator can block the patient from using the aggregator's service. For example, if a patient does not show up for one or more appointments, the aggregator can lock (permanently or temporarily) the patient out of the aggregator's service. Alternatively, if a patient cancels too many appointments in a short time frame, the aggregator can also lock them out of the service.

In accordance with another aspect of the invention, the aggregator collects and provides on its website patient feedback regarding the practitioners with whom appointments were booked. This patient feedback is limited to patients that have actually booked appointments through the aggregator and attended the appointment. For example, after the aggregator confirms that a patient attended a booked appointment, the patient is sent an email by the aggregator asking them to rate the practitioner. The responses to such email are collected by the aggregator and may be provided as patient feedback to future perspective patients. For example, the feedback may be displayed on the webpage which displays the search results. The feedback solicited may be standardized (by category of input and options for response) by the aggregator, to facilitate comparison. The aggregator may also compile or temporarily escrow the reviews (e.g. until an appropriate number are received) to provide a more reliable assessment of each practitioner, and also to prevent one possibly non-representative review from unfairly skewing traffic (the number of a subsequent bookings) to or away from a practitioner.

In accordance with another aspect of the invention, the aggregator's website allows patients to filter practitioners based on insurance plans, i.e. the aggregator's website informs the prospective patient whether the practitioner is considered "in network", "out of network", or "out of network but the practitioner files the paperwork". The aggregator provides the practitioner groups with a master (predetermined) list of insurance companies and plans from which the practitioner can designate which plans they participate in, again, in network, out of network, and out of network but practitioner files the paperwork.

In accordance with another aspect of the invention, the aggregator displays the available appointment times in a particular format. In one embodiment, the display includes for example seven (7) days horizontally displayed along the top, various time slots listed below each day with each time slot being an active link for selecting the time slot, and a button available to select other dates such as the next week and/or the previous week. In another embodiment, the display includes a vertical listing of the practitioner groups meeting the search criteria, with the available appointment times horizontally displayed across the page, adjacent the applicable practitioner. Again, a multi-day (e.g. weekly), layout may be provided for the available time slots.

In accordance with another aspect of the invention, the aggregator sends patients one or more reminders before every appointment. The aggregator may send a reminder immediately when the appointment is booked, and then follow it up with a reminder a week before the appointment, one day before the appointment, and one hour before the appointment.

These and other features of various embodiments of the invention are further described below.

Introduction

In accordance with one embodiment of the invention, FIG. 1 illustrates schematically a centralized marketplace 10 for healthcare services across multiple practice groups A, B, C, D, . . . in which a centralized service provider (aggregator) 12 provides available appointment times from the plurality of different practice groups 14 to the plurality of prospective patients 16, and wherein the prospective patients are not required to have a pre-existing relationship with any one of the practice groups. The aggregator provides a network based service to the patients and practitioner groups, e.g., the aggregator's server 13 provides a web interface 13 to each of the patient computers 17, and can also communicate electronically via email 14 to each of the patient computers 17. The aggregator's server 13 also communicates (e.g., online and web-based) with each of the practice groups 14 via the practice group servers 15 for retrieving available appointment times from each of the practice groups in order to book and confirm appointments with the prospective patients 16. Suitable hardware, communication protocols and software languages for implementing the systems and methods of the various embodiments of the invention described below are readily known to those skilled in the art and any discussion herein is not meant to limit the scope of the invention.

The network 10 includes an aggregator server 13 which executes the various software processes of the present invention, and communicates with a plurality of patient computers 17 located at remote locations from the server 13. The server 13 and patient computers 17 are coupled together via the Internet and communicate with one another using standard communication protocols, such as TCP/IP. The server 13 can be any type of server, including, but not limited to Windows Server 2003, Unix, Linux and Apple OS type servers.

Figure 1B:
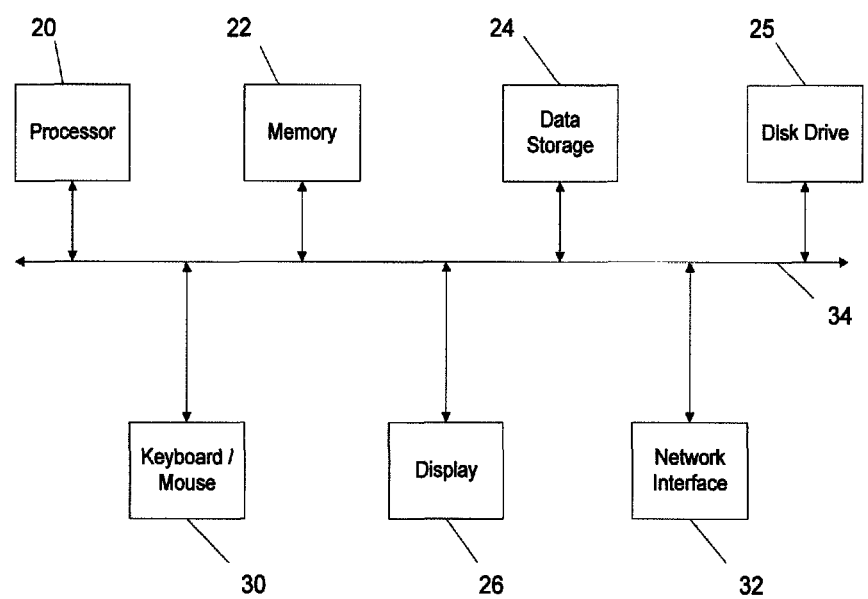
FIG. 1b is a block diagram of an exemplary computer on which the software product(s) of the present invention may be executed.

Referring to FIG. 1b, a block diagram is shown of a server 13 used to execute the software processes of the present invention. Server 13 includes a processor 20, memory 22, data storage 24, disk drive 25, computer display 26, keyboard/mouse 30, and a network interface 32. The components are coupled together and communicate via a system bus 34. The software product of the present invention is loaded into data storage 24 and during operation is transferred into (e.g. RAM) memory 22 and is executed by the processor 20. Information regarding the software product is presented on display 26. A user may manipulate the software product and enter commands into the server 13 using the keyboard/mouse 30. The network interface 32 couples the server 13 to the Internet 18, or whatever type of network is used to connect the server 13 with the patient computers 17 and the practice group servers 15. Further, the server may communicate with a storage array or storage network (e.g. SANS) if there is a need to access large amounts of data. A database of patient records, practice group (practitioner) records, and associated scheduling records, may be implemented as a relational database and search engine with, for example, Microsoft's Active Server Page technology, SQL server technology, Database Artisan Software, or database products from Oracle Corp., Redwood Shores, Calif.

The software product may be implemented as various modules, e.g. a web module, a database module, an email module, and standard application program interfaces (APIs). The web module may include a set of templates and icons to enable the creation of web-pages. It may include other tools that allow a user to create browser-friendly, interactive websites. These tools enable the creation of dynamic hypertext web-pages to be accessed by the patients and practice groups.

The database module may include a relational database and search engine. The records, fields, search queries and other features of the database are described below and suitable alternatives would be apparent to a person skilled in the art.

The email module enables emails to be sent to patients and the practice groups from server 13. The emails can be sent manually by a person operating the server 13 or they can be automatically generated by the server 13. For example, the email module can be configured to automatically query the database module and send email messages to entities identified in the database module.

The software product includes standard APIs so data and other information can be exchanged with other software systems.

Each of the practice groups 14 has a practice group server 15 for communicating with the aggregator's server 13. Each practice server may include the groups own patient management software (PMS) and any other database of information used by the practitioners in that group. As described below, the aggregator may install software on the practice group servers for uploading available appointment times to the aggregator's database and otherwise automating and synchronizing the appointment calendars of the practice groups and the aggregator. The aggregator and practice group servers are coupled via the Internet. The relevant appointment booking information may be stored on one or both of the aggregator and practice group servers.

The database maintained by the aggregator includes records of booking information for each of the practice groups and their respective practitioners, as well as each patient who establishes an account with the aggregator. These records will be described further below in the various embodiments.

Practitioner Side Operation

Figure 2A:
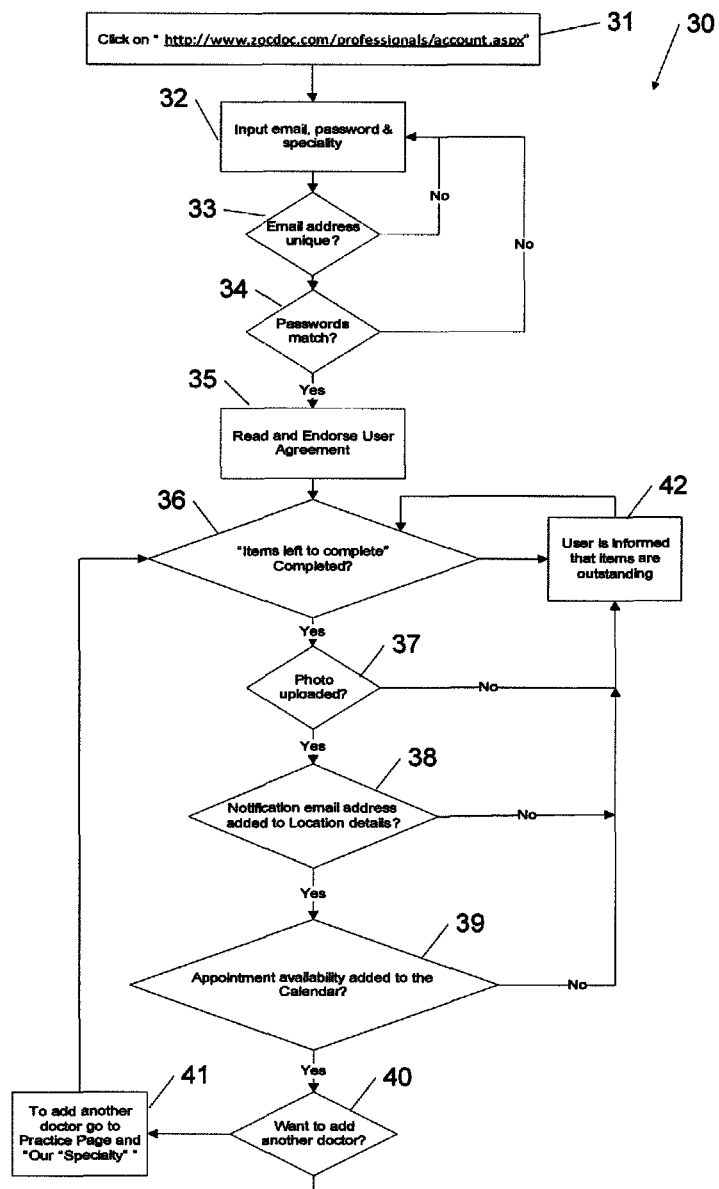
FIG. 2 (parts 1 and 2) is a flow diagram illustrating the operation and sequence of one embodiment of a software product of the present invention, for creating a practitioner group (client) account.
Figure 2B:
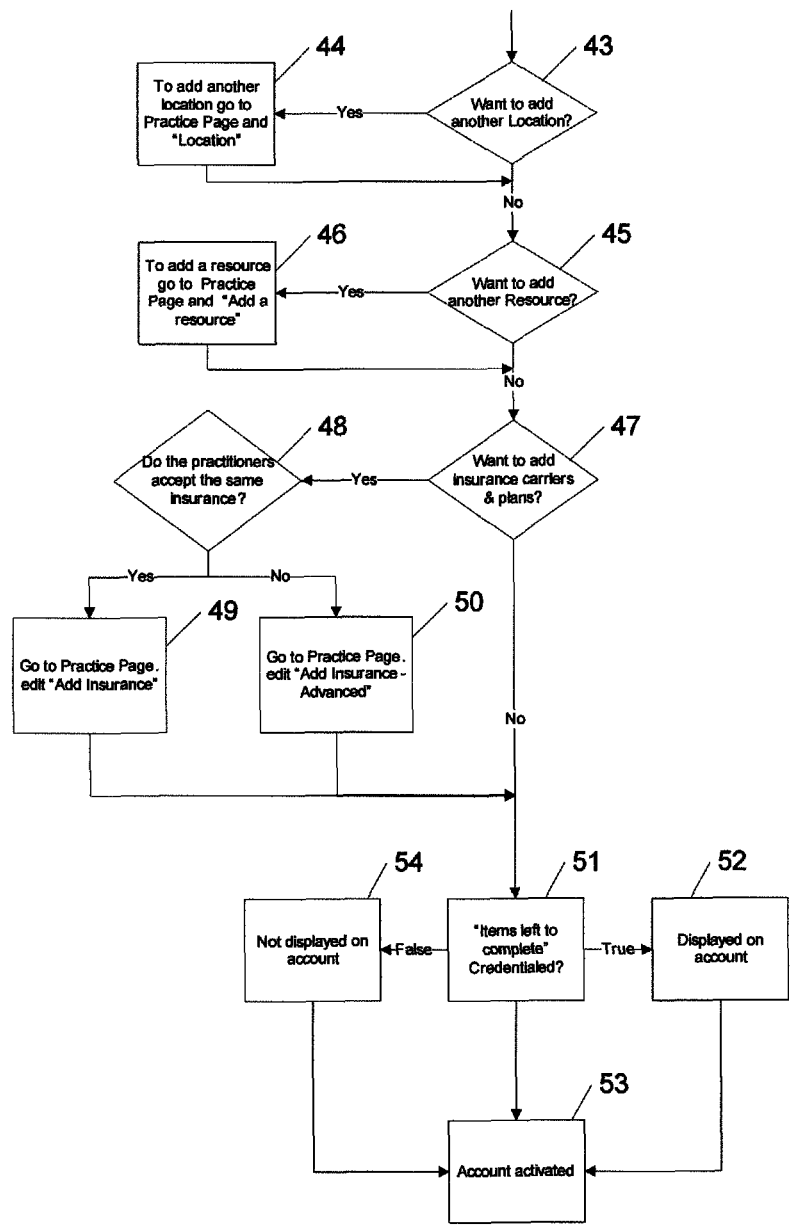
Figure 3:
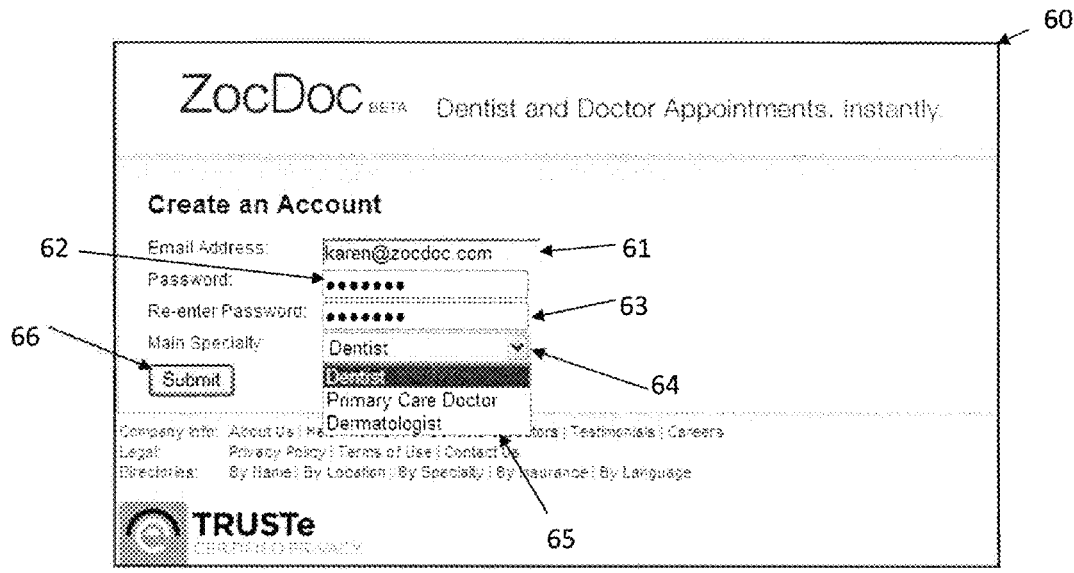
FIG. 3 is an exemplary webpage enabling a practice group (client) to create an account.

FIG. 2 is a flow diagram illustrating the operation and sequence of one embodiment of the software product of the present invention for creating a practitioner group (client) account. According to the process 30, initially the portal website of the aggregator is accessed (Box 31) and a client selects the client access page for creating an account. The client inputs an email address, selects a password, and identifies one of the aggregator-defined medical specialties (Box 32) for entry in the respective data entry fields 61-64 of the corresponding "create an account" webpage 60 as shown in FIG. 3. The pull down menu 65 of the "main specialty" window, includes aggregator defined categories from which the client is required to select, in order to standardize the search process for prospective patients. The exemplary specialties include dentist, primary care doctor, dermatologist, ophthalmologist, orthopedic surgeon, and ear-nose-throat specialist. The client hits the submit button 66 to enter the selected data. The aggregator then confirms (in Decision Diamonds 33 and 34) that the client's email address is unique and that the input passwords match; if they do, the client is presented with a user agreement (Box 35) which the client is required to execute to create an account with the aggregator (Box 35). If the email address or passwords are defective, the client is returned to prior webpage (Box 32) with a notice to correct the respective entries.

Figure 4:
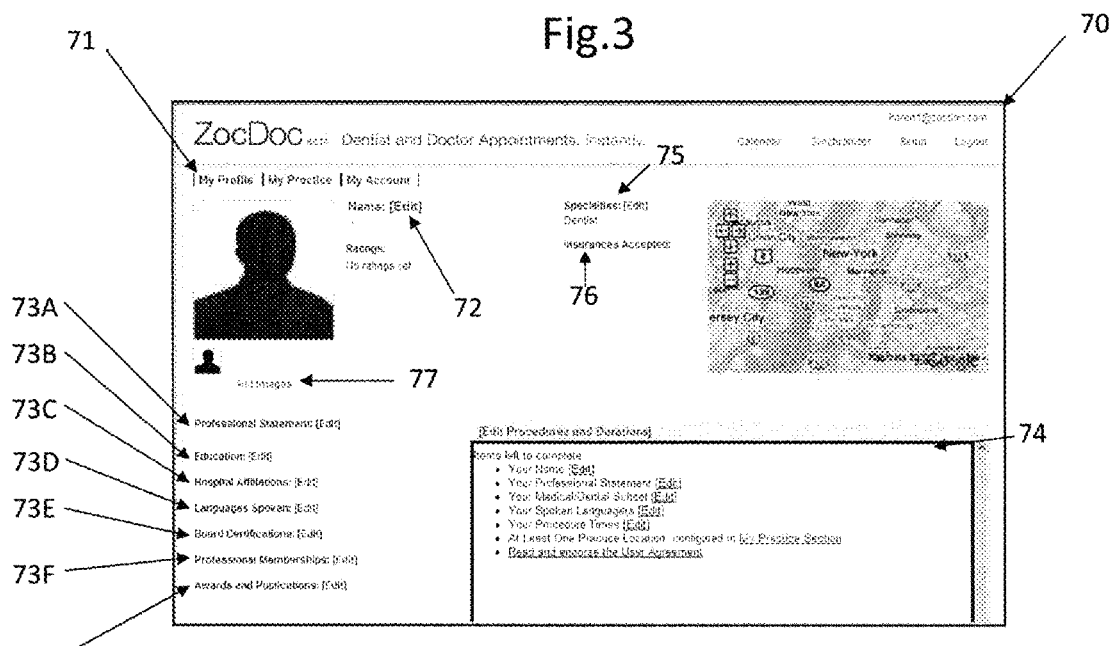
FIG. 4 is an exemplary webpage enabling a client to enter individual practitioner profile information.

Once the account has been opened, the client is led through a series of requests (Decision Diamonds 36-47 in serial order), to provide information that will be used in the patient search of practitioners. As illustrated in the corresponding webpage 70 of FIG. 4, the client is prompted to provide client profile information 71, such as name 72, professional statement 73a, education 73b, hospital affiliations 73c, languages spoken 73d, board certifications 73e, professional memberships 73f, and awards and publications 73g. The client is also prompted to provide (not shown) practice times, and at least one practice location in the reference table of account information. The client is informed if items are outstanding (Box 42) and returned to Decision Diamond 36 to provide the outstanding items (as noted in window 74). Additional information requested includes: a specialty 76; insurances accepted 77; a photo 77 (Diamond 37); notification email address for receiving emails from the aggregator (Diamond 38); and appointment availability to be added to the aggregator's calendar (Diamond 39). The step of adding appointment times is discussed further below with reference to FIGS. 5-6. If the client is a practice group with multiple practitioners (e.g. doctors), the client is asked whether additional practitioners will be registered (Diamond 40) and if so, the process returns to create another account for the additional practitioner (Box 41) and the client is requested to fill in the same profile information for the additional practitioner (return to Diamond 36).

Figure 5:
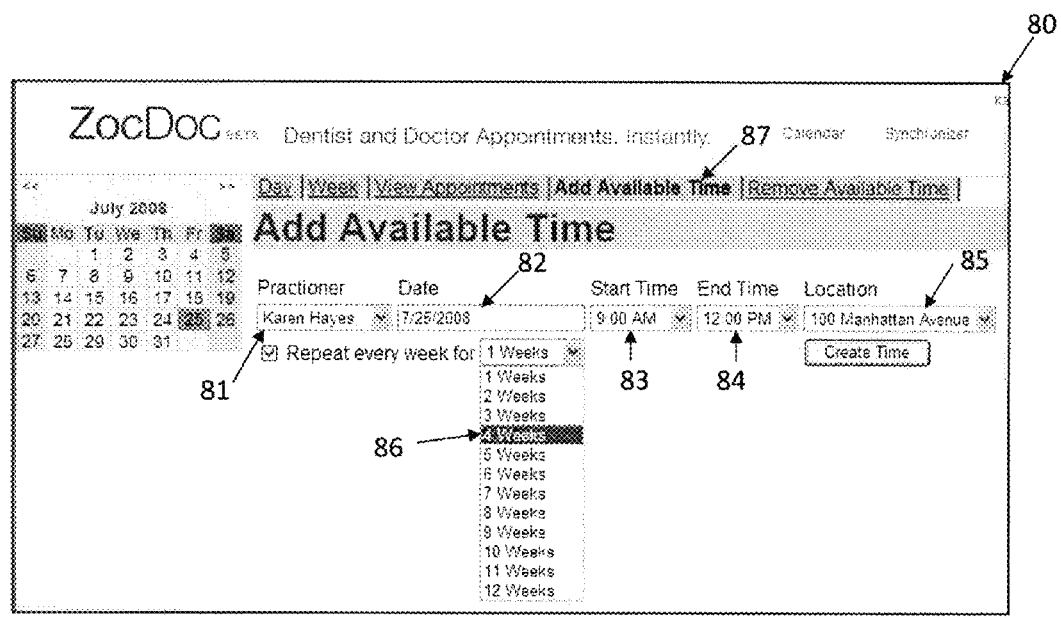
FIG. 5 is an exemplary webpage enabling a client to enter available appointment times for a respective practitioner.
Figure 6:
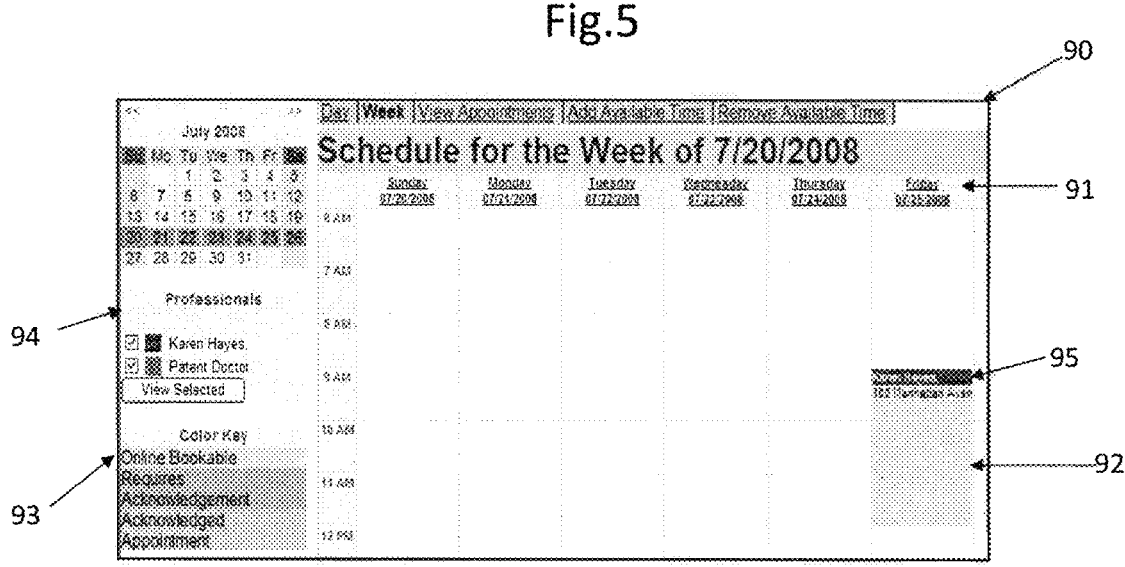
FIG. 6 is an exemplary webpage showing a client the appointment availability for respective practitioners in a calendar format.

FIGS. 5-6 illustrate two webpages (from the aggregator's website) for entry of available appointment time. In the first webpage 80, for the practitioner identified in the practitioner data field 81, the client selects a date (shown in the date field 82), and enters a start time (shown in the start time field 83) and an end time (shown in the end time field 84) of a continuous time period during which appointments may be made with this practitioner, for a particular practitioner location (identified in the location field 85). If desired, the client also selects this available time period for future dates, by using the pull down menu 86 of periodic future times (here illustrated in number(s) of weeks). Having selected Friday, July 25, 2008 from 9:00 a.m. to 12:00 p.m. as an available continuous time period, and by clicking on the submit (add available time) button 87, the added time will now appear in the scheduling calendar window 91 of the webpage 90 of FIG. 6, highlighted as a block 92 for the respective date/time during the week of July 20, 2008, i.e. denoting the available time block 92 in green according to the color key 93 for "online bookable" time. Because this practice group has multiple professionals (identified in the "Professionals" window 94), the time block 92 also includes at the top 95 an identification of the associated practitioner having the available time period. This process can then be repeated for additional dates and time periods, and additional practitioners.

Figure 7:
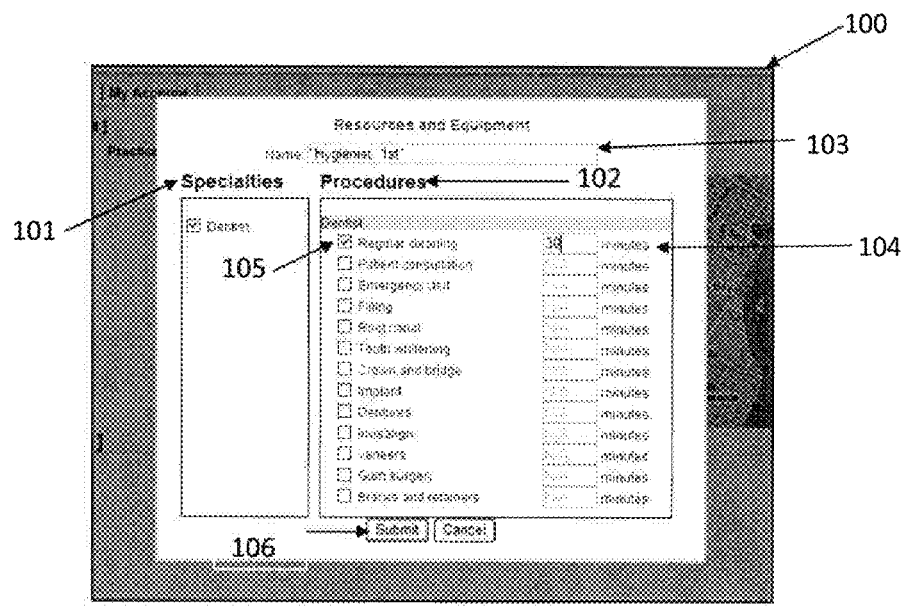
FIG. 7 is an exemplary webpage enabling a client to identify resources for a particular procedure.

Returning to FIG. 2, the client is prompted to add an additional geographical location (Diamond 43), if the practice group has such additional locations; the client is then directed to another webpage (not shown) to enter the relevant location information (Box 44). The client is then prompted to add/identify resources (Decision Diamond 45 and Box 46), in addition to the previously identified practitioners. One example of this process is illustrated with the webpage 100 of FIG. 7, wherein the practitioner, designated as a dentist (in window 101), has added as a resource (in window 103) a hygienist to perform or assist in performing the selected procedure, here a "regular cleaning" having an allocated time of 30 minutes (in the data field 104). The client is required to select from the aggregator defined list (of standardized procedures in window 102) one of the defined procedures, but the client can define an individualized practitioner time (in minutes) for the procedure. As a result, during the search process, patients will be able to select from among the same aggregator defined group of procedures, but the available appointment times for a designated procedure may vary by individual practitioner (designated time in field 104 for the procedure). The client then hits the submit button 106 to enter the identified resource information. Other resources may include equipment or office space required for the procedure, to enable the practitioner to link a particular piece of equipment or office with a designated procedure, in order to insure that when patient books an appointment both the human resources and non-human (e.g. equipment and office space) resources are available at the selected appointment time.

Figure 8:
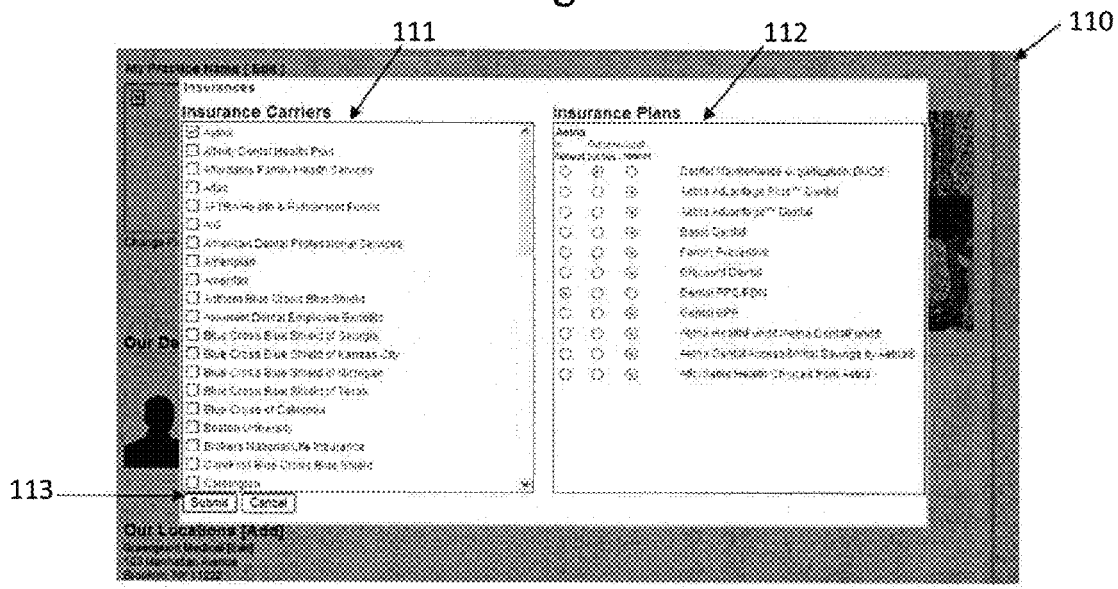
FIG. 8 is an exemplary webpage allowing a client to enter (only once) the same insurance information for each practitioner in the practice group.
Figure 9:
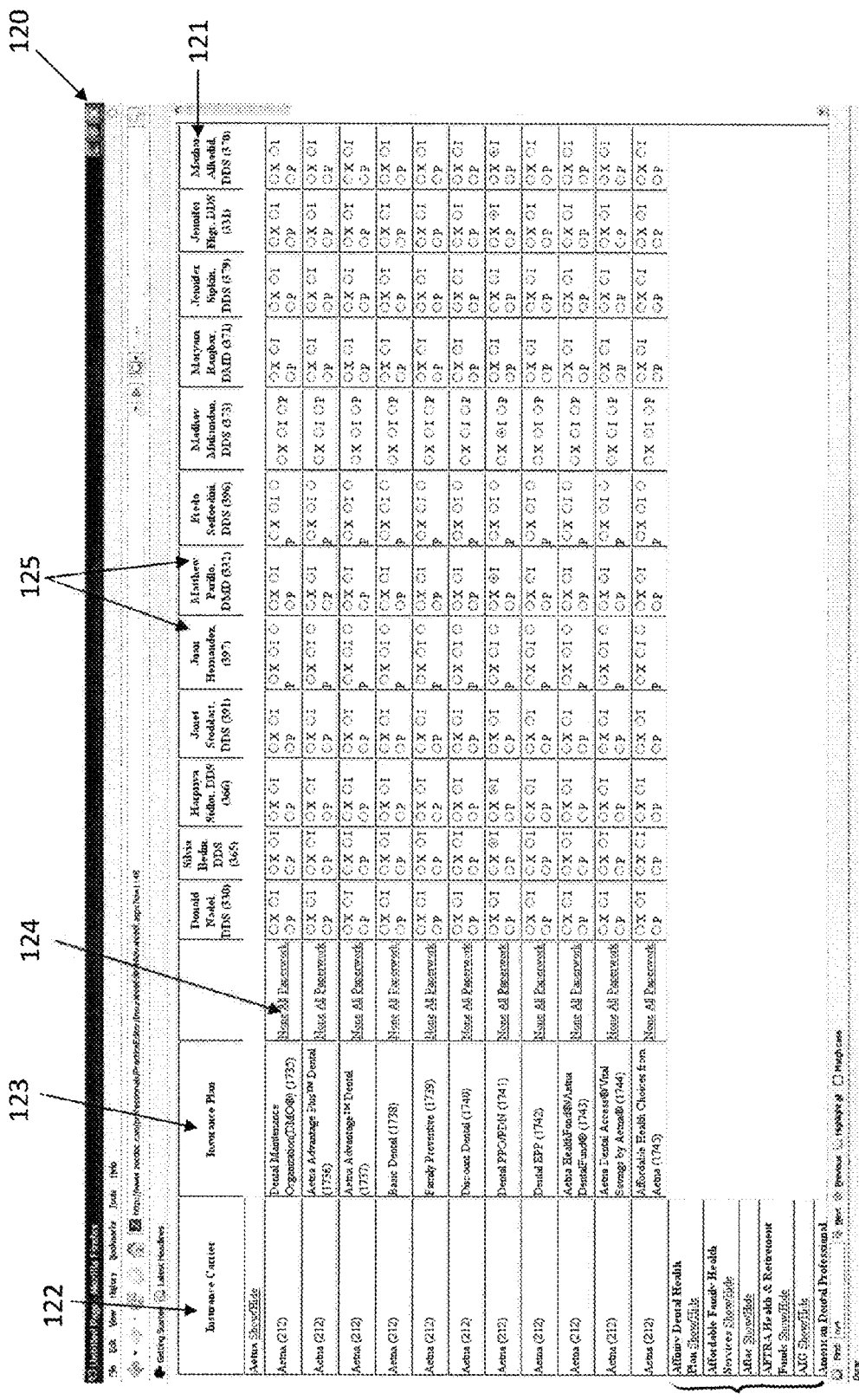
FIG. 9 is an exemplary webpage enabling a client to enter different insurance information for different practitioners in the practice group.

Returning to FIG. 2, the client is now asked to provide insurance information (Diamond 47). If all of the practitioners in a specific practitioner group accept the same insurance, the client is sent to a webpage 110, illustrated in FIG. 8, which allows the client to enter once the same information for each practitioner in the group. A window 111 identifies a list of standard insurance carriers, from which the client is required to select (by checking the associated box) the one or more applicable carriers, and a second window 112 lists standard insurance plans, from which to select the applicable plans. In the embodiment shown, three selection circles allow the client to identify each plan as: in network, out of network but client handles paperwork, or out of network. The client then hits the submit button 113 to enter the relevant insurance information for the group. In contrast, if individual practitioners in the group have different insurance carriers/plans, then the client is sent to (Box 50) the webpage 120 illustrated in FIG. 9 with a more advanced display of options for identifying the relevant insurance carriers and plans for each practitioner. A window 121 displays a grid including insurance carrier selections 122 as a first column, insurance plan selections 123 in the second column, a third column 124 for indicating whether the practitioner will or will not provide paperwork for the insurance carrier/plan and in the remaining columns 125, an identification of each of the practitioners in the client group. Additional information and selection options for insurance may also be provided, such as a list of insurance carriers 126.

Returning to FIG. 2, after the client submits the appropriate insurance information, the aggregator reviews the entered client information to determine if any items are left to be completed (Box 51); if there are uncompleted items, these are displayed on the client account page (FIG. 4) for editing, and once completed, the account is activated (Box 53). If no items are outstanding (Box 54), the account is activated (Box 53).

Figure 10:
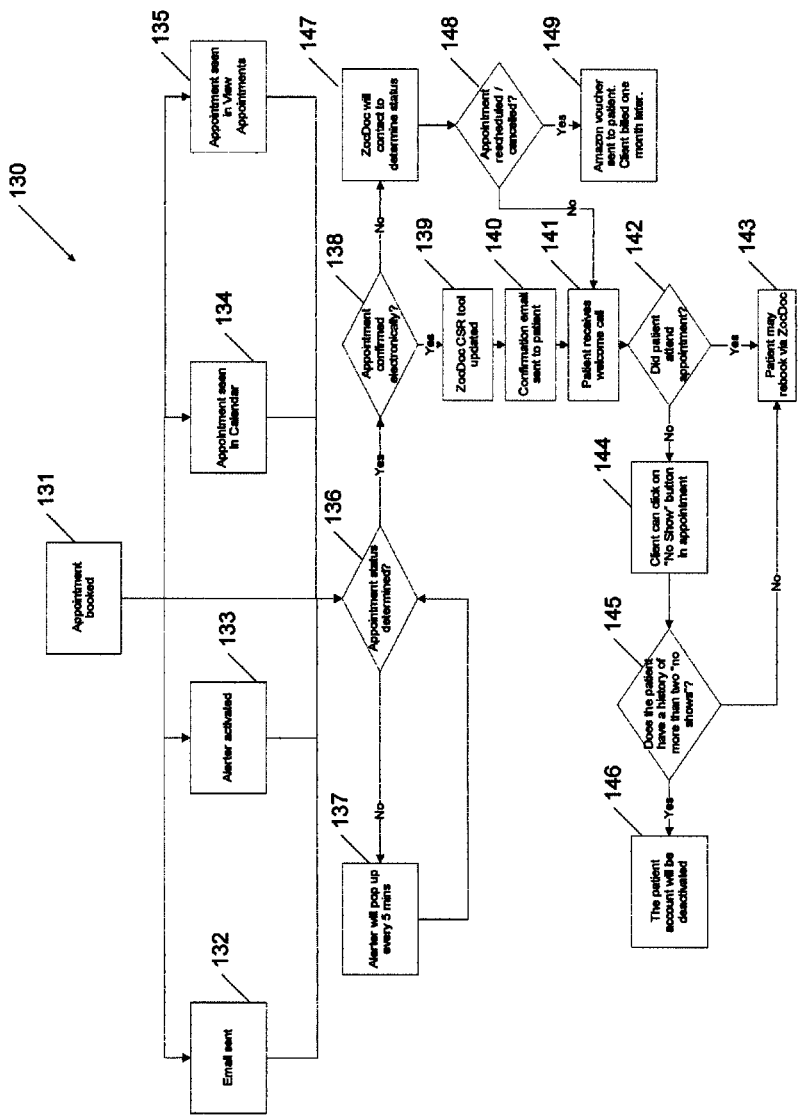
FIG. 10 is a flow diagram illustrating the operation and sequence of one embodiment of a software product of the present invention, for client notification of a booked appointment.

FIG. 10 is a flow diagram illustrating of the operation and sequence of one embodiment of the software product of the present invention for client notification of appointments. According to the process 130, when a patient books an appointment with the aggregator (Box 131), the client can be notified by one or more communication mechanisms until the appointment status is confirmed (Decision Diamond 136). Depending upon the notification options selected by the client, the client may be sent an email (Box 132), with appointment details similar to that shown in FIG. 30.

Another notification option is to notify the client via an alerter (Box 133). An alerter is an application which is installed on the client's computer which hides itself in the task bar notification area until a new appointment is booked with the client. When this occurs, the application presents itself (e.g. as a popup window) on the client's computer screen, alerting the client of this new appointment and the need to confirm it. The alerter software checks the aggregator's web server for updates (new appointments booked) regularly. For example, every 5 minutes the alerter may request an alerter HTML page with new appointments from the aggregator's web server. If the page contains unconfirmed appointments, a popup window appears on the client's computer screen. This may be instead of or in addition to the email notification previously described.

Figure 11:
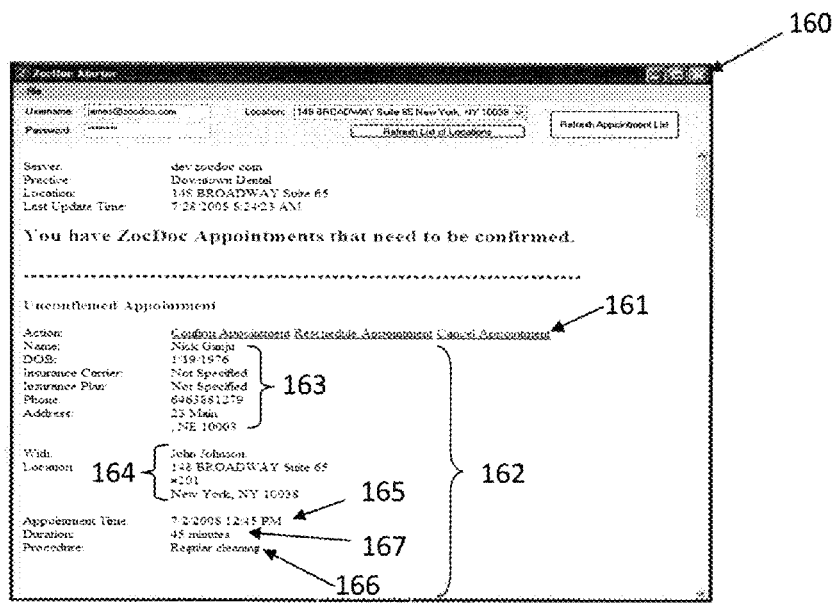
FIG. 11 is a exemplary pop-up window which appears on a client's computer screen showing unconfirmed appointments that need to be confirmed by the client.

FIG. 11 illustrates such a popup window 160 which appears on the client's computer screen when unconfirmed appointments have been made, and that need to be confirmed by the client. The window includes text information 162 concerning the patient, practitioner and procedure. In this example, the text includes various identification information 163 regarding the patient, i.e., name, date of birth, insurance carrier, insurance plan, phone number and address, and further includes information 164 regarding the practitioner and practice group location for the booked appointment. The text also identifies the appointment date and starting time 165, the procedure 167, and duration time 166 for the associated procedure. The email includes a plurality of highlighted links 161 by which the client can confirm or alter the appointment status, namely: confirm appointment; reschedule appointment; cancel appointment. The aggregator is thus notified, by the client's response via the selected link, whether the appointment status is confirmed (Diamond 136).

Figure 12:
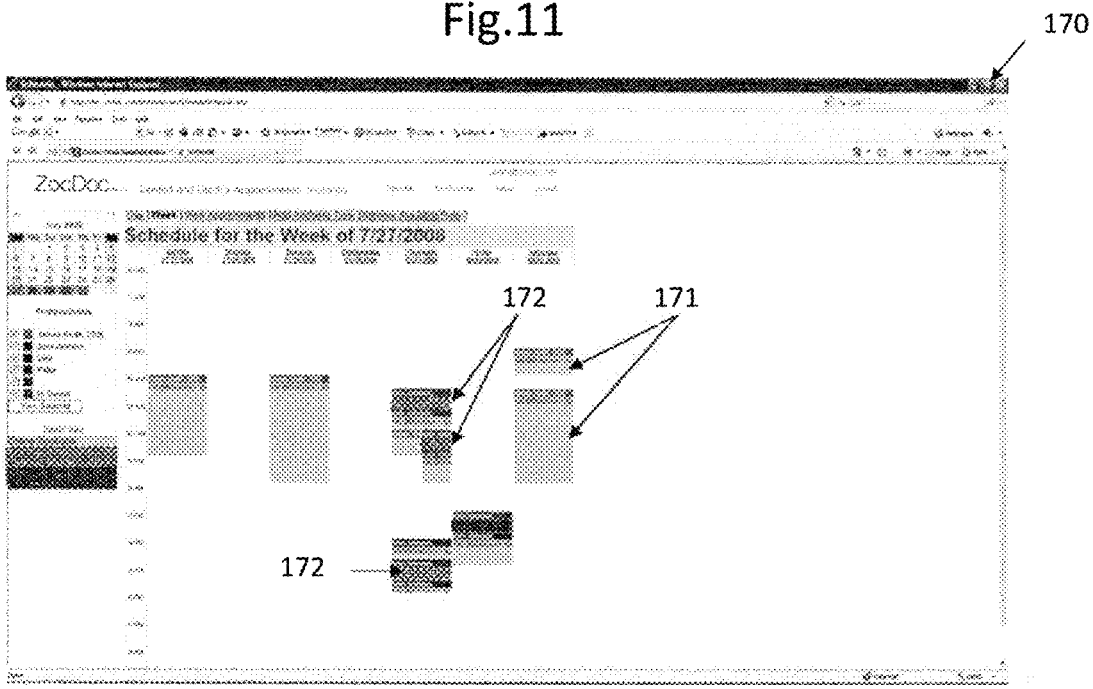
FIG. 12 is an exemplary webpage showing a client, in calendar format, the status of various appointments.

In a further alternative, client notification is via an appointment which appears in the client's scheduling calendar (Box 134), an example of which is illustrated in FIG. 12. FIG. 12 is a webpage display 170 (on the aggregator's website) similar to that shown in FIG. 6, but now includes, in addition to multiple available appointment times 171 (in color key green), a plurality of booked appointments which require acknowledgement 172 (in color key orange). Again, each of these time blocks appear in a grid of time (vertically displayed) and day of the week (horizontally displayed), for one week. The client is prompted to select among a series of links (not shown, but similar to links 161 in FIG. 11) to confirm the appointment or reschedule or cancel the appointment. If the appointment is confirmed, the time block in the calendar 170 is changed from orange to blue, indicating that the appointment has been confirmed by the client.

Figures 13, 14:
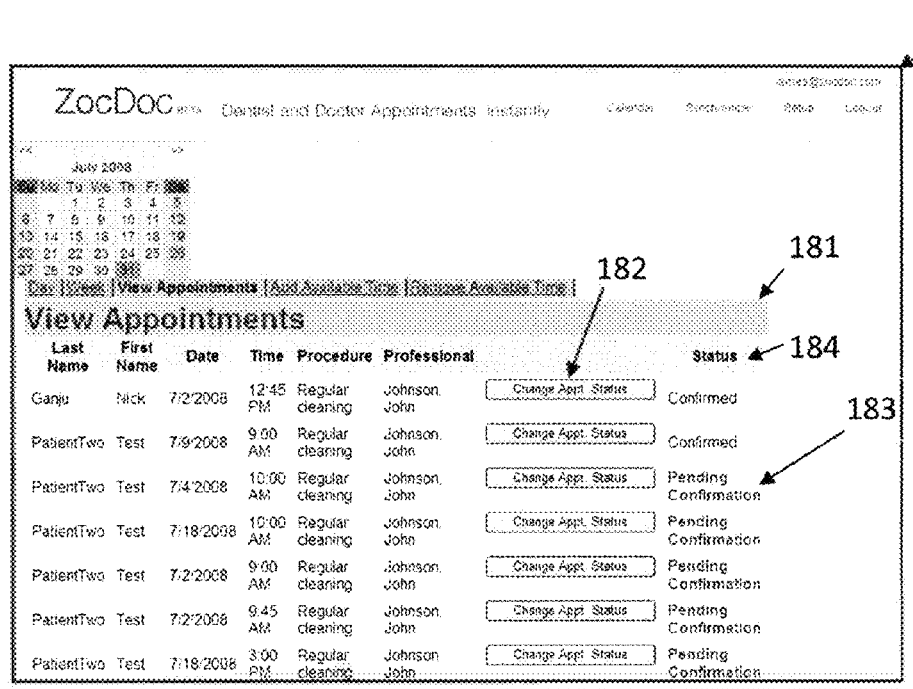
FIG. 13 is an exemplary webpage showing a client the notification details of various appointments.
FIG. 14 is an exemplary webpage showing a client the appointment details of a confirmed appointment.

In a further alterative (Box 135), client notification details of an appointment can be viewed in the client's view appointment webpage 180 as illustrated in FIG. 13. Here, a window 181 displays the booked appointments for each of the practitioners in the group, in date order, including the time, procedure, practitioner, and status. The status can be changed by clicking on the link (button) 182 for the associated record entry. If an appointment has not yet been confirmed (e.g. the third record 183), the status is highlighted in the last column 184 as pending confirmation. Once confirmed, the status is indicated as confirmed (see record number two) and no longer highlighted.

Figure 15:
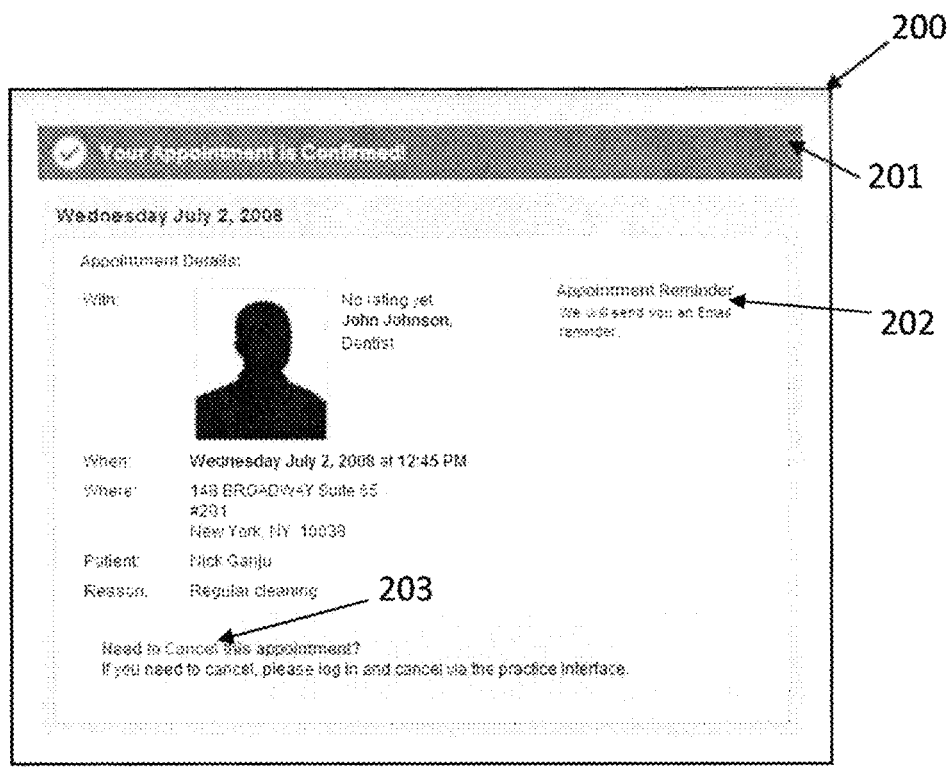
FIG. 15 is an exemplary webpage showing an appointment confirmation.

Returning to FIG. 10, the aggregator will monitor the status of unconfirmed appointments and notify the client appropriately (Decision Diamond 136). For example, the client may be notified via the alerter (popup window) every 5 minutes (Box 137). Once the client has confirmed the appointment electronically (Decision Diamond 138), then the aggregator updates its database and website pages (Box 139) and notifies the patient (Boxes 140-141). FIG. 14 illustrates a web-page 190 on the aggregator's site, available to the client, for displaying the appointment details of an appointment which has been confirmed electronically. It includes the patient information 191, practitioner information 192, and the appointment date/time/duration/procedure 193. FIG. 15 illustrates an appointment confirmation webpage 200 which notifies the patient that the appointment has been confirmed 201 and which includes the details of the appointment in window 202, including the date, time, location, procedure, patient, practitioner and procedure information. A link 203 is provided for the patient to change the appointment, if necessary.

Returning to FIG. 10, the process updates the aggregator's database to include the confirmed appointment information and a CSR tool displays the updated booking information (Box 139). In the CSR display (management console for customer service representatives) 210 shown in FIG. 16, the confirmed bookings for each of a plurality of clients are displayed in a grid 211, with the clients listed vertically (in alphabetical order) down the page, for convenient viewing by (an employee of) the aggregator. Each client entry includes, underneath an identification of the practice group name and telephone number 212, a series of data field headings 213 displayed horizontally across the page. These include: client ID, appointment time initiated, closing appointment time, practitioner name, additional practitioner resources (if any), followed by patient information. The patient information includes the user's first and last name, email address, telephone number(s), status of the patient ID, status of the patient's telephone number, reason for the visit, patient's IP address from which the appointment was booked, geographic location of the IP address including country and region (e.g. state). As described hereinafter, the aggregator may use the patient location information to perform an integrity check on booked appointments to detect bogus appointments.

Returning to FIG. 10, the aggregator sends the patient an email confirming the appointment (Box 140); the patient may also receive a welcome call from the client or aggregator (Box 141). Details of the confirming email will be described in the following sections.

If the appointment has not yet been confirmed by the client after some predetermined amount of time, the aggregator will contact the client to determine the status (Box 147). If the client needs to reschedule or cancel the appointment (Decision Diamond 148) then the aggregator will send the patient a consolation gift, here an Amazon voucher, and the client will be billed for this voucher (Box 149). This will discourage clients from canceling or rescheduling appointments which have been booked by the aggregator. Otherwise, the appointment is confirmed and the patient receives a welcome call from the client (Box 141).

Figure 17:
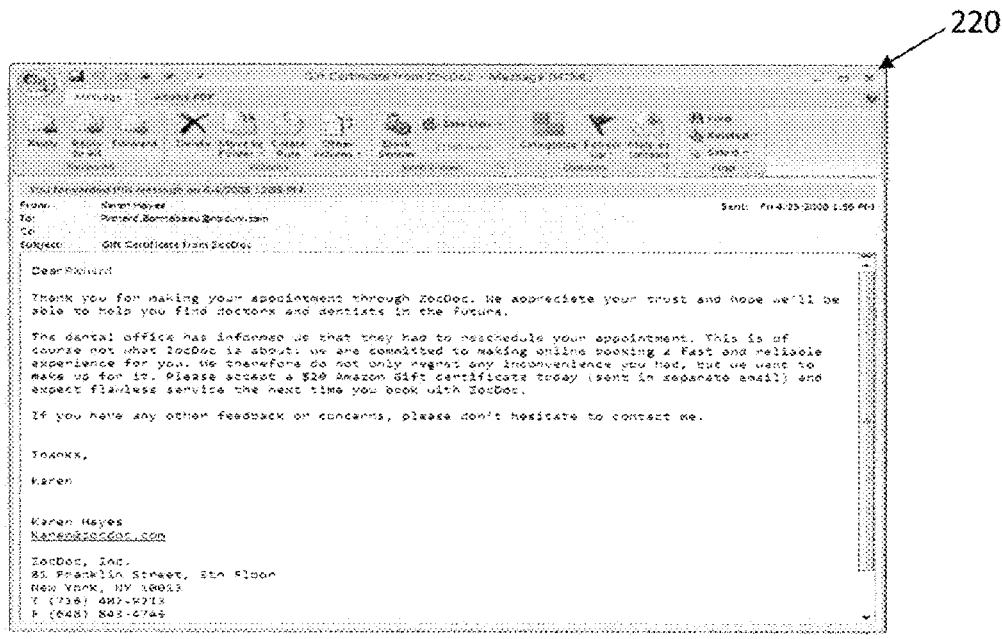
FIG. 17 is an exemplary email message notifying a patient that the practitioner needs to reschedule the appointment.

FIG. 17 shows an example of an email message 220 sent to a patient, indicating that the practitioner needs to reschedule the appointment, inviting the patient to reschedule a new appointment, and sending (by separate email) an Amazon gift certificate to the patient to compensate for the inconvenience of having to reschedule.

The aggregator also tracks the patient experience, in order to ensure that patients are satisfied with the appointments being booked with the aggregator. The aggregator determines, e.g., via the client, whether the patient attended the appointment (Decision Diamond 142). If yes, the patient will be allowed to rebook additional appointments via the aggregator (Box 143), as the patient has established a record of showing up for booked appointments. If not, the client identifies the patient as a no-show (Box 144), for example using the link 194 on the client appointment details page 190 of FIG. 14. If it is determined that this patient has a history of no-shows, for example more than two no-shows (Decision Diamond 145), then the aggregator will deactivate the patient's account (Box 146); the patient's phone number may also be blacklisted to prevent the patient from opening another account in the future. If not, the patient is allowed to book additional appointments with the aggregator (Box 143).

Figure 18:
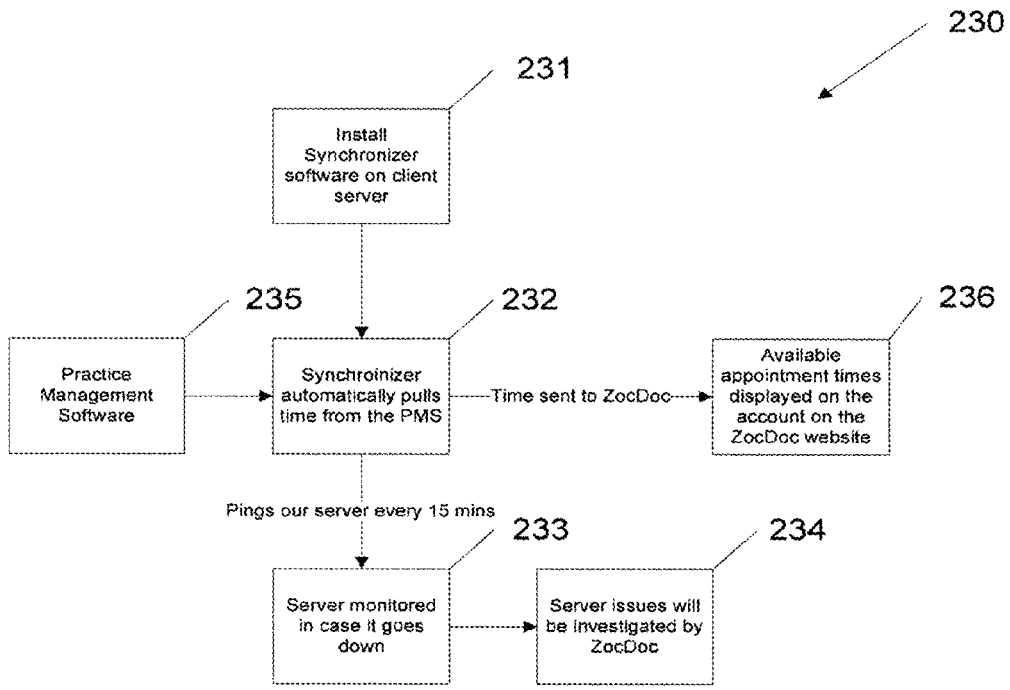
FIG. 18 is a flow diagram illustrating the operation and sequence of another embodiment of a software product of the present invention, for synchronizing the appointment records of the aggregator and the clients.

FIG. 18 is a flow diagram illustrating the operation and sequence of another embodiment of the software product of the present invention, for synchronizing the appointment records of the aggregator and the clients. As previously described, a synchronizer application may be installed on the client's computer 15 (Box 231). The synchronizer automatically pulls time (Box 232) from the client's practice management software PMS (Box 235). This time is sent to the aggregator's server 13, enabling the aggregator to process and update the available appointment times displayed for this practitioner account on the aggregator's website (Box 236). Thus, if new appointments are added to the client's PMS, these times are removed from the list of available times in the aggregator's calendar. If appointments in the client's PMS are canceled, these times are made available again in the aggregator's calendar. In order for the aggregator to know it is receiving appointment updates from the client, the synchronizer will periodically ping (e.g., every 15 minutes) the aggregator server 13 and if communication ceases (Box 233), the aggregator will investigate the communication failure with the client (Box 234) to resolve the same.

Figure 19A:
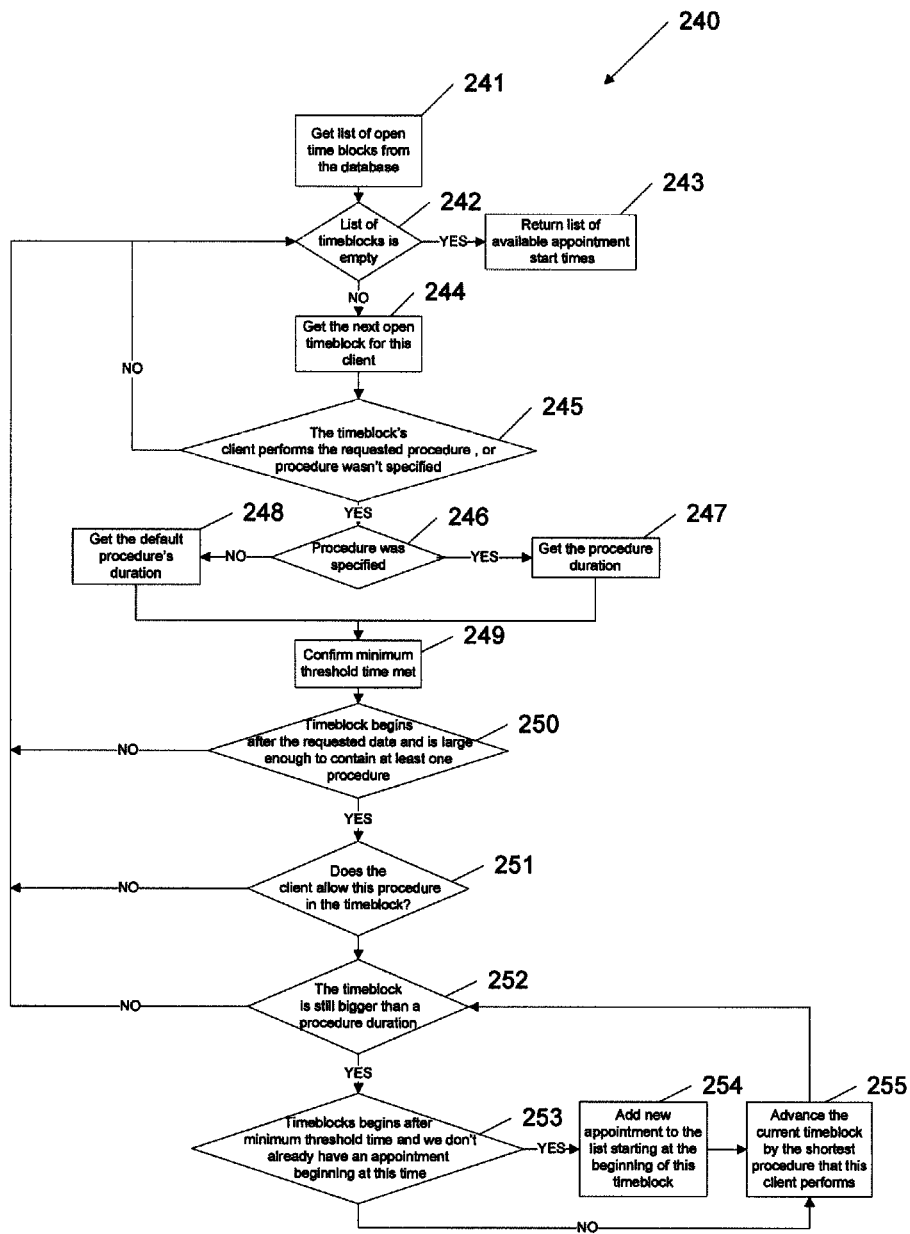
FIG. 19a is a flow diagram illustrating the operation and sequence of one embodiment of a software product of the present invention, for generating a list of available appointment time slots.

According to another aspect of the invention, FIG. 19a is a flow diagram illustrating the operation and sequence of one embodiment of the software product of the present invention, namely a process for time slot splicing of the available appointment times. This process 240 is used to determine the available appointment times that can be offered to patients from each client. Open time slots are stored in the aggregator database as larger time blocks and the process splits the time blocks into individual appointment starting time slots, each of the length designated by the client as the shortest procedure time for the associated practitioner. This provides the patient with greater flexibility in selecting appointment start times, without leaving the practitioner with unusable (too small) segments of available time. It allows the aggregator to offer the patient a greater number of possible appointment times, for each individual practitioner.

Referring to FIG. 19a, the process 240 obtains a list of open time blocks from the aggregator database 12 (Box 241). Each time block is processed (in the loop shown below Diamond 242), until all blocks have been processed and the process returns a list of available start times (Box 243). The process gets the next open time block for a given practitioner (Box 244) and determines whether the practitioner (for this time block) performs the requested procedure, or if no procedure was specified by the patient (Diamond 245). If the patient has designated the procedure (Decision Diamond 246), then the method uses the procedure duration previously identified for this practitioner (Box 247). If the patient has not identified the procedure (Diamond 246), then the process uses a default procedure time (Box 248). The method then confirms that a minimum threshold time is met (Box 249), i.e., there is enough time to allow the practitioner to confirm the booking. If it is determined that the time block (being processed) meets the confirmation threshold, it is then determined whether, if the patient has selected an appointment date/time, the time block includes time within the requested date/time and whether the time block is big enough to contain at least one designated procedure (Diamond 250). If yes, the method determines whether the practitioner has specified (allows) this procedure in the relevant time period (e.g., all resources are available for this procedure at the time and/or the doctor has not limited the times at which he will perform certain procedures) (Diamond 251). If yes, and it is determined that the time block is bigger than the procedure duration (Diamond 252), the process then determines whether the time block begins after the minimum threshold time and that there is no previously booked appointment overlapping at this time (Diamond 253). If these conditions are met, the appointment is added to the list starting at the beginning of this time block (Box 254). Then the beginning of the time block is advanced by the shortest procedure time specified by the practitioner for any procedure the practitioner performs (Box 255). This maximizes the number of available start times that can be offered to the patient, while not leaving the practitioner with an unusable (too short) gap between appointments. Otherwise (if the conditions of Box 253) are not met, the process proceeds directly to advance the time block by the shortest procedure duration that this practitioner performs (Box 255). As indicated, this process will increase the available appointment start times offered to the patient. Also, the time blocks stored in the aggregator's database need not be spliced into smaller time slots (for a given procedure) until a specific procedure is requested. This reduces the size and complexity of the aggregator data records.

FIGS. 19b illustrates one embodiment of a group of database records 235 in the aggregator database. Each record (row) includes data fields for, in addition to an initial record id (key) 237:

| | |
|---|---|
| practice id (specialty) | 236a |
| client id (practitioner) | 236b |
| client location id | 236c |
| procedure id | 236d |
| start time | 236e |
| end time | 236f |
| status | 236g |
| booking id | 236h |
| duration | 236i |

Open time blocks have a status of null and a booking id of null. The last 4 records identify booked appointments.

Figure 20A:
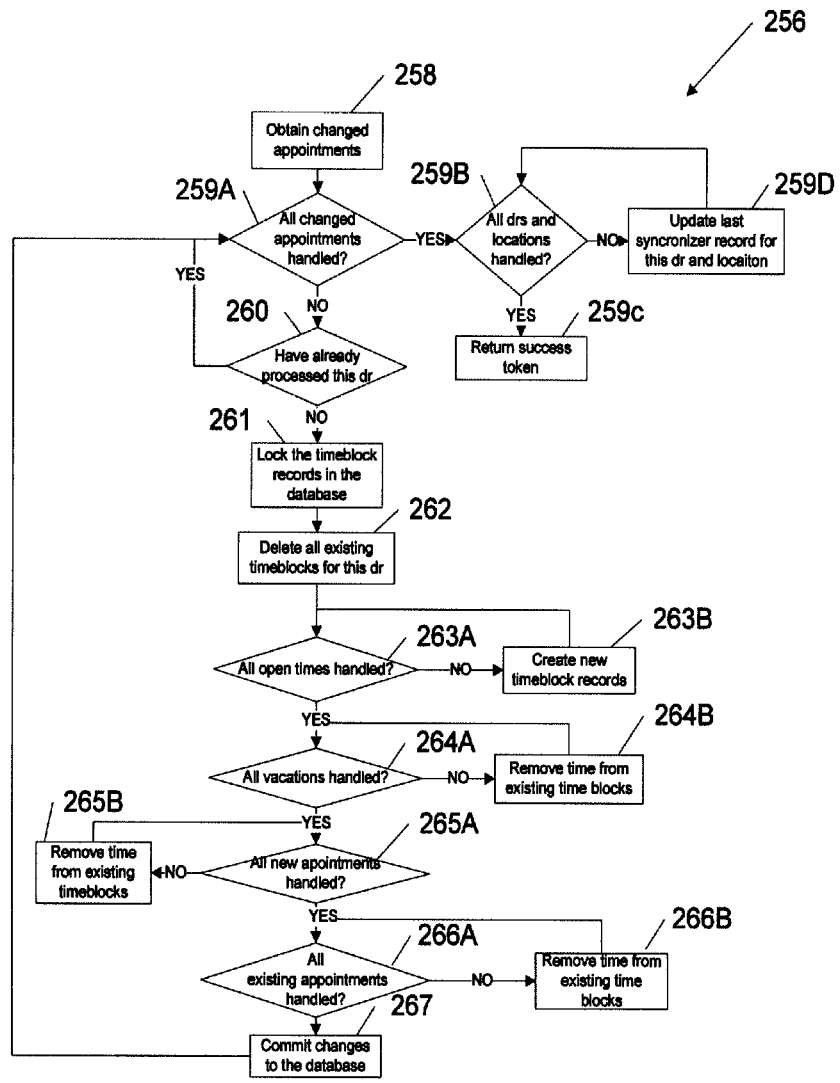
FIG. 20a is a flow diagram illustrating the operation and sequence of another embodiment of a software product of the present invention, for processing appointment changes.

As previously described, a synchronizer application installed on the client's computer will retrieve all changed (new and canceled) appointment data from the client's appointment booking system and send it to the aggregator's software in order to update the aggregator's client calendar of available time slots. As illustrated in the flow chart of FIG. 20a, the process 256 obtains the changed appointments from the client synchronizer (Box 258). Then, looping through each changed appointment (Diamond 259a) and each practitioner (doctor) in the practice group (Diamond 260), the time block records in the aggregator database are locked (Box 261). The method then deletes all existing time blocks for this practitioner (Box 262), and for all open times (Diamond 263a), creates new time block records (Box 263b). From these new records, the client designated vacation times are removed from the existing time blocks (Diamond 264a and Box 264b). For new appointments made by the client (not through the aggregator) (Diamond 265a), these appointment times are removed from the existing time blocks (Box 265b). For all existing appointments for the client made through the aggregator (Diamond 266a), these times are removed from the existing time blocks (Box 266b). Then, the changes are committed to the database (Box 267). The time block records may then be unlocked. Once all practitioners (e.g. doctors and practitioner locations) have been handled (Diamond 259b), and the last sync record updated for this doctor and location, the process is completed (Box 259c)

Figure 20B:
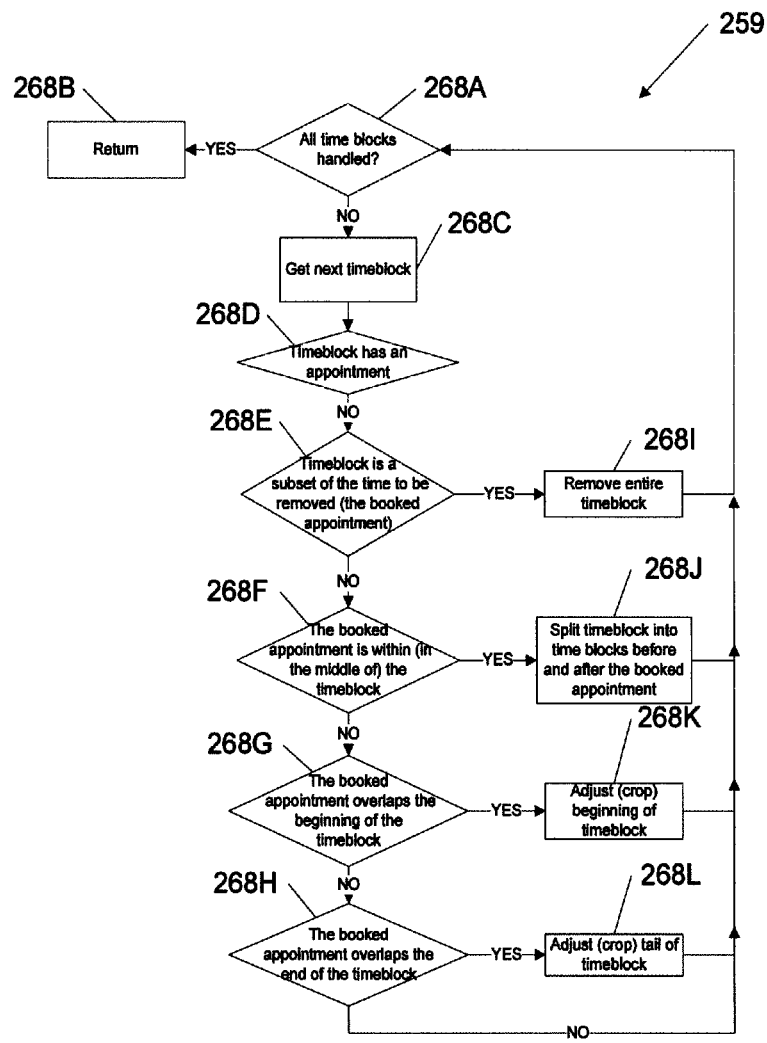
FIG. 20b is a flow diagram illustrating the operation and sequence of one embodiment of a software product of the present invention, for removing booked appointment time from the appointment records of the aggregator.

As further illustrated in FIG. 20b, a procedure 269 is provided for handling the removal of booked appointment time (from the available time blocks). The process obtains the time blocks to be handled (e.g. appointments booked by the aggregator and by the clients manually (by telephone)) and determines whether all such time blocks have been handled (Diamond 268a). If true, the process ends (Box 268b). If not the process gets the next time block to be handled (Box 268c). It is determined (Diamond 268d) whether the time block is a subset (within) the booked appointment time period (Diamond 268e), and if so, the entire time block is removed (Box 268i). Otherwise, it is determined whether the booked appointment time period (Diamond 268f) is within the time block, i.e. in the middle of it (Diamond 268f), and if yes, the appointment time is split into two time blocks one before and one after the appointment time which are added separately to a list of existing time blocks to also be checked (Box 268j). Otherwise, if the booked appointment overlaps the beginning of the time block (Diamond 268g), the head of the time block is cropped (Box 268k). Otherwise, if the booked appointment overlaps the tail of the time block (Diamond 268h), the tail of the time block is cropped (Box 286l). The process loops through (returns to Diamond 268a) until all time blocks are handled.

Figure 21:
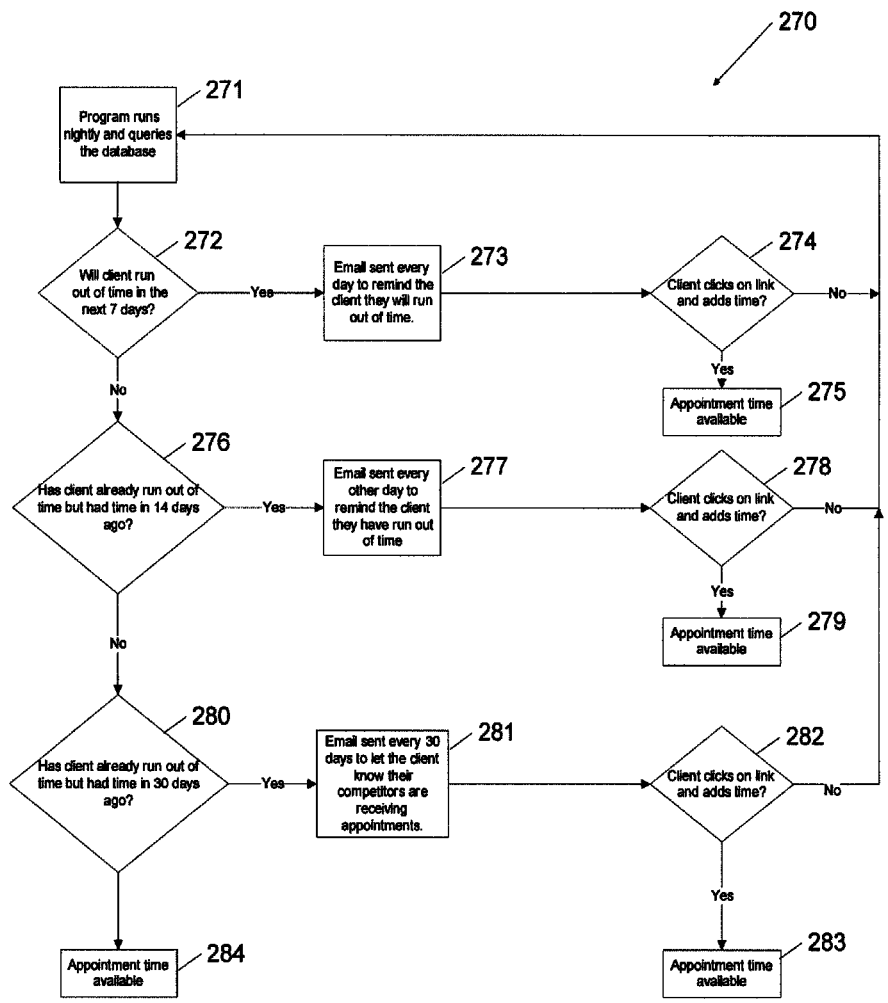
FIG. 21 is a flow chart illustrating the operation and sequence of another embodiment of a software product of the present invention, for reminding the client to add new available appointment times to the aggregator's calendar.

FIG. 21 is a flow chart illustrating the operation and sequence of another embodiment of the software product of the present invention, for reminding the client to add new available appointment times to the aggregator's calendar. This is another mechanism for keeping the aggregator and client calendars in sync and enhancing the available appointment times offered to patients.

This process runs on the aggregator server 13, querying the aggregator database to determine which clients need to add appointment times. Depending on the results, a variety of email reminders can be sent to the clients.

In this process 270, a program runs nightly on the aggregator server 13 and queries the database (Box 271). It first determines whether a client will run out of available appointment time in the next 7 days (Diamond 272). If yes, an email is sent by the aggregator to the client every day to remind the client that they will run out of time (Box 273). In response, the client can click on a link to add more time (Diamond 274). If desired, the client enters additional available appointment times (Box 275). It is next determined whether the client has already run out of time, but had available time in the calendar up to 14 days ago (Diamond 276). If yes, an email is sent to the client every other day to remind the client they have run out of time (Box 277). The client can click on a link in the email if it wants to add time (Diamond 278), and then add available appointment time (Box 279). The process determines whether the client has already run out of time but had time in 30 or more days ago (Diamond 280). If yes, the client is sent an email every 30 days to let the client know its competitors have been receiving appointments via the aggregator (Box 281). A client can click on a link in the email if it wants to add time (Diamond 282), and then add available appointment time (Box 283). If the answers to the three determinations (Diamonds 272, 276 and 280) are negative, then the client is considered to have available appointment time (Box 284).

Patient Side Operation

The following methods and systems illustrate embodiments of the invention in which a prospective patient is enabled to search for and select an available appointment. Also described are methods and systems for the patient to create an account with the aggregator, to enable the booking of an appointment, and processes for location verification (to identify and eliminate possible bogus appointments) and the collection and processing of patient feedback to provide credible evidence of the utility of the search and selection process.

Figure 22:
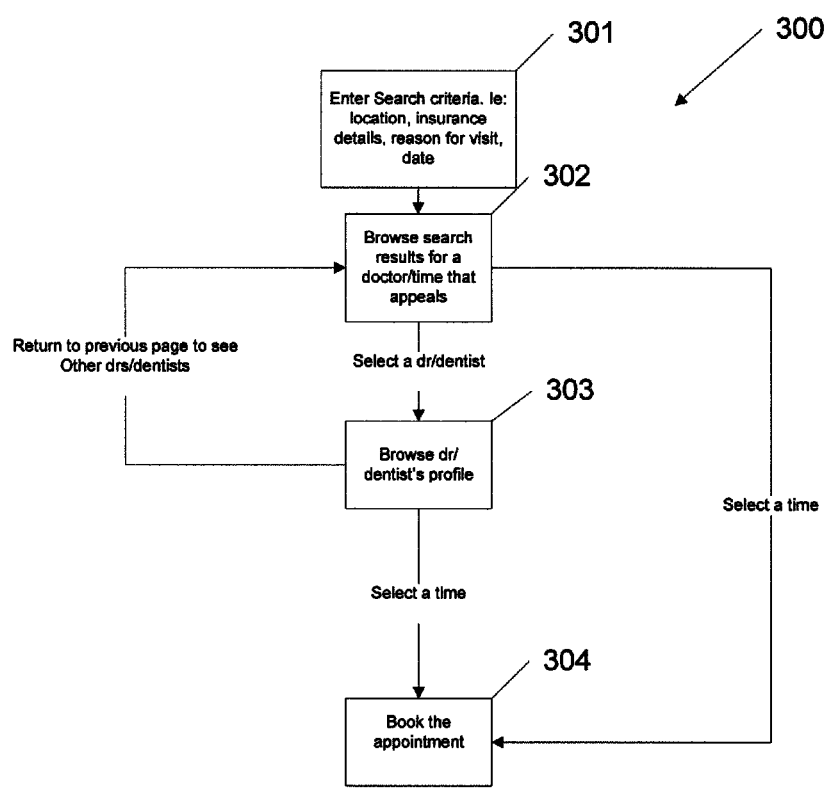
FIG. 22 is a flow diagram illustrating the operation and sequence of an embodiment of a software product of the present invention, enabling a patient to search for and book an appointment.
Figure 23A:
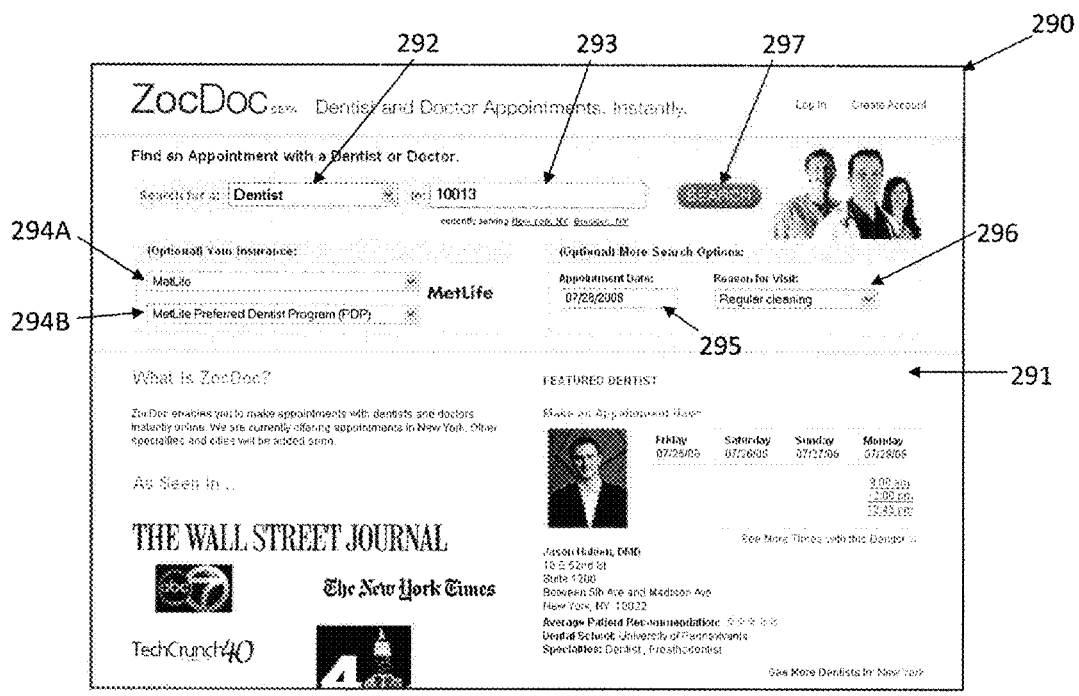
FIG. 23a is an exemplary webpage enabling a patient to enter a search criteria.

FIG. 22 is a flow diagram illustrating the operation and sequence of an embodiment of the software product of the present invention, enabling a patient to search for and book an appointment. According to the process 300, the patient accesses the aggregator's website and enters the search criteria, namely the desired practitioner specialty and location, but also preferably one or more of the insurance details, procedure, and desired appointment date (Box 301). FIG. 23a illustrates a webpage 290 on the aggregator's website for entering the search criteria. A window 291 includes data entry field 292 for entering the desired specialty of the practitioner (shown as a pull down menu) from a set of aggregator defined specialties. Another window 293 is a data field for entering the patient's desired geographic location for the appointment, here a zip code. Another data field 294a (with a pull down menu) has designated choices which allows the patient to select an insurance carrier, and another data field 294b has designated choices which allows the patient to select an insurance plan. A further data field 295 allows the patient to enter the desired appointment date, and a further window 296 has a pull down menu for the patient to select among aggregator defined procedures. The patient then clicks a search button 297 to begin the search.

Figure 23B:
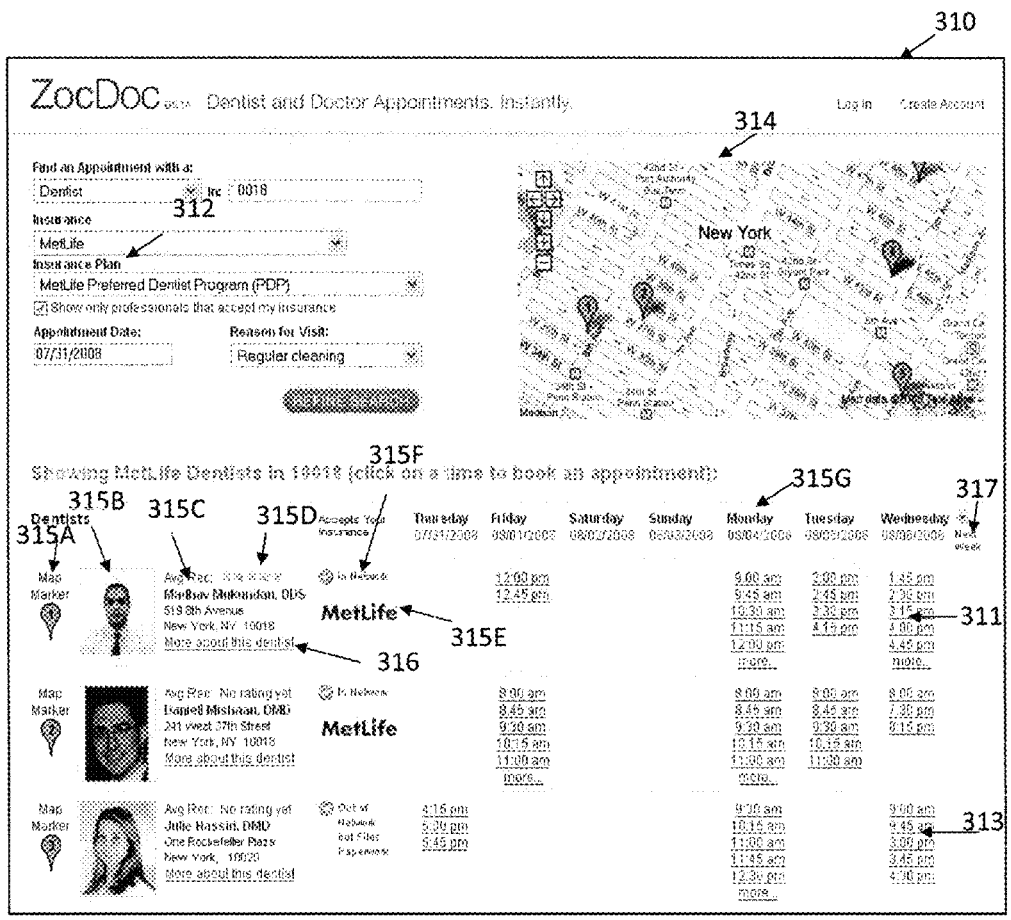
FIG. 23b is an exemplary webpage for displaying the search results to the patient.

The search is conducted on the data in the aggregator's database of available appointment times. The search results are presented to the patient, enabling the patient to browse the results for a doctor and times that appeal to the individual patient (Box 302). FIG. 23b illustrates an aggregator's webpage 310 for displaying the search results 311 below the inputted search criteria 312. A grid is provided of identified practitioners having available appointment times meeting the search criteria. In this embodiment, the available times 313 for each practitioner are provided horizontally across the page for one week. For each practitioner the results include: a location designator (map marker number 315a) which correlates to the map marker shown in the graphic display 314 of the geographic region encompassing the practitioners having available times in the requested location; a photo 315b of the practitioner; a text identification 315c of the physician's name and street address; patient feedback 315d for this practitioner; a link 316 to request more information on the practitioner; an identification 315e of the insurance plan requested by the patient and whether this practitioner would be considered within the network of the patient's insurance plan 315f; and a grid 315g of the next 7 days sequentially presented across the page, with available appointment start time slots 313 listed under each of the relevant days (aligned with the respective practitioner). The time slots are links 313 which a patient can select by simply clicking on the link. In addition, the patient is provided with a link 317 to browse additional appointment times available in the future, such as the next week.

Figure 24:
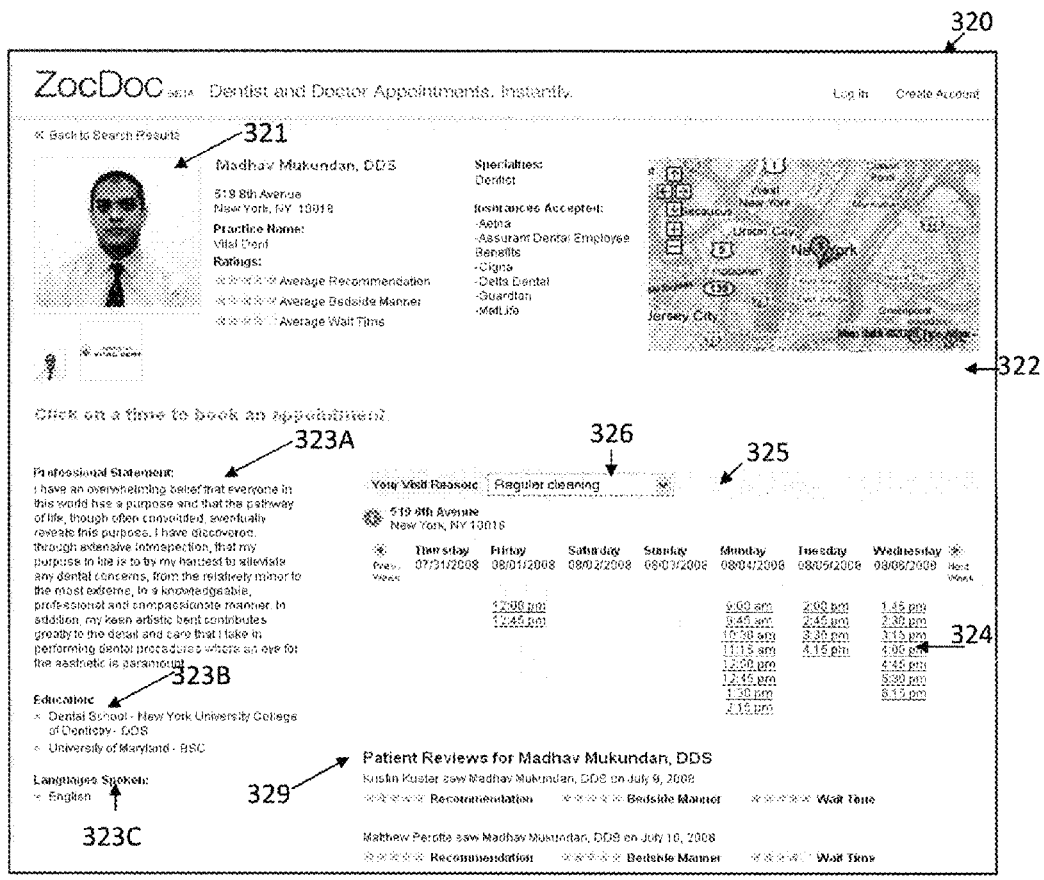
FIG. 24 is an exemplary webpage of a practitioner profile for review by a patient.

Returning to FIG. 22, the patient selects a desired practitioner and is then presented with a webpage on the aggregator's site which enables the patient to browse the selected practitioner's profile (Box 303). An example of such a profile is shown in the webpage 320 of FIG. 24. The profile of the selected practitioner includes the background information previously provided by the client/practitioner group, as well as the results of the search and patient feedback on this practitioner which has been processed and presented by the aggregator. The upper portion 321 of the webpage shows the practitioner photo, name and geographic location, name of the practice group, prior patient ratings, specialty and insurance accepted, and again a graphic display 322 of practitioner's location with the map marker. Below this, the webpage further includes a professional statement by the practitioner 323a, a description of the practitioner's education 323b and languages spoken 323c. It then includes a summary 325 of the search criteria (e.g. procedure 326) and results available (appointment times 324), enabling the patient to click on an available appointment time 324 (in the same manner as FIG. 23b). The presentation of the patient reviews 329 will be described in a later section.

Returning to FIG. 22, if a patient wishes to browse the profiles of other practitioners having available appointment times meeting the search criteria, the patient returns to the prior webpage of FIG. 23a (Box 302). The patient can thus select an available appointment time from either of the webpages shown in FIGS. 23b and 24 to book an appointment (Box 304).

Figure 25:
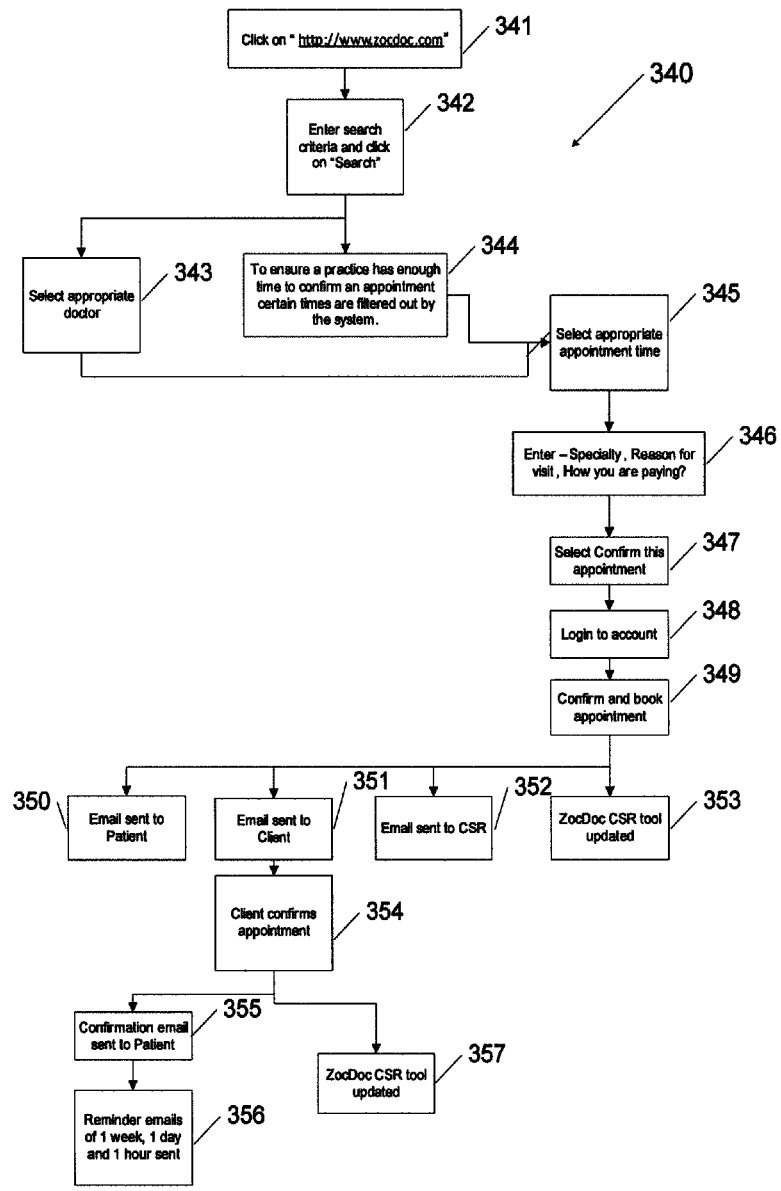
FIG. 25 is a flow diagram illustrating the operation and sequence of an embodiment of a software product of the present invention, providing greater detail on a process for booking an appointment.
Figure 26:
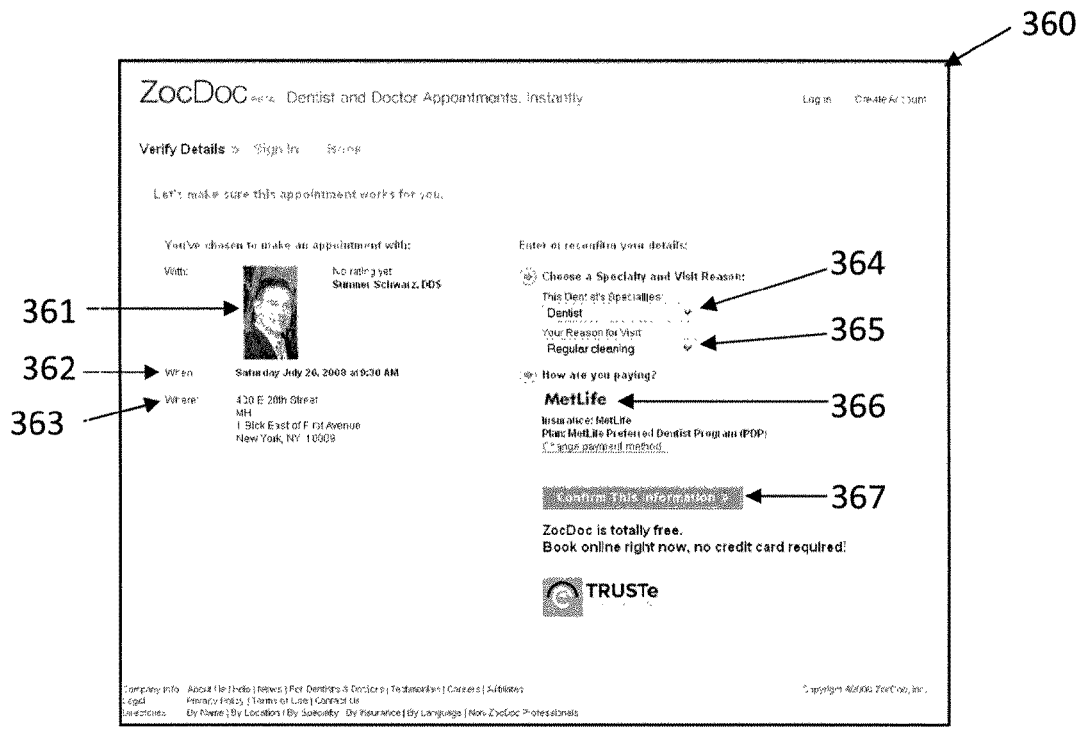
FIG. 26 is an exemplary webpage enabling a patient to confirm the details of a requested appointment.

FIG. 25 is a flow diagram illustrating the operation and sequence of an embodiment of the software product of the present invention, providing greater detail on the process of booking an appointment. According to the process 340, the patient accesses the aggregator's website (Box 341), enters the search criteria on the aggregator's webpage, such as that shown in FIG. 23(a), and clicks on the search button (Box 342). The aggregator software conducts a search of the aggregator database and returns the results in a webpage, such as that shown in FIG. 23(b). The patient selects an appropriate doctor (Box 343) and an appropriate appointment time (Box 345). In processing the search request, the process determines whether the practice group has enough time to confirm an appointment and if not, filters out such available appointment time (Box 344). After selecting the appointment time, the patient is presented with the webpage, such as the webpage 360 shown in FIG. 26, asking the patient to confirm the selected details of the appointment, including the practitioner 361, date and time 362, practitioner location 363, specialty 364, reason for visit (procedure) 365, and method of payment 367, (e.g. via a selected insurance plan). The patient is then asked to click on a button 367 to confirm this appointment (Box 347).

Figure 27:
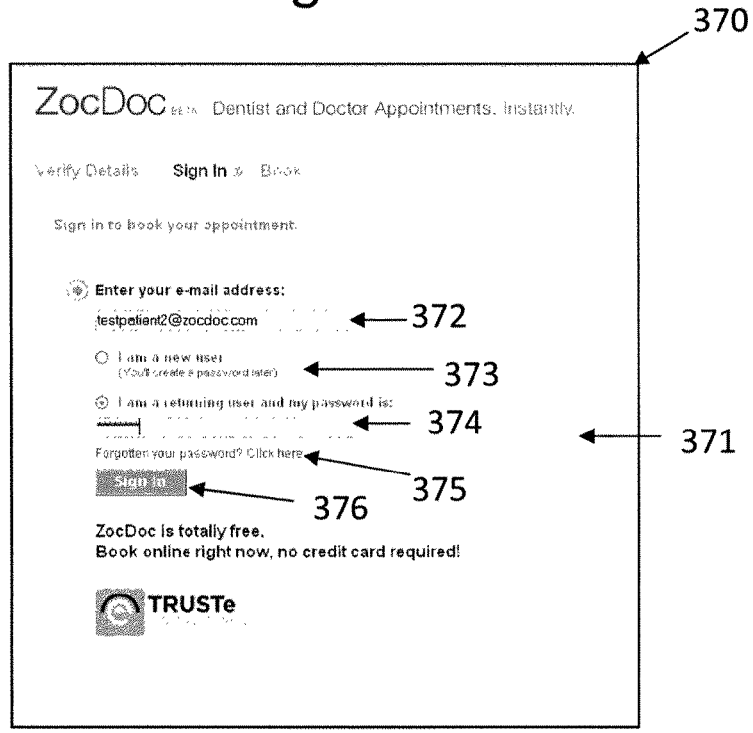
FIG. 27 is an exemplary webpage enabling a patient to open an account.

In order to confirm the appointment, the patient is next presented with a webpage 370 for logging into the patient account (Box 348), as shown in FIG. 27. A sign in window 371 is presented including a data field 372 requesting entry of the patient's email address, and data field 373 asking whether the patient is a new user (in which case the user will need to create an account and password) or a returning user (in which case the patient enters his patient password in field 374). If the patient has forgotten his password, a link 375 is provided for sending the patient his password. After entering the above account information, the patient clicks the sign in button 376.

After confirming the patient's login information, the aggregator presents the patient with a webpage for confirming and booking the appointment (Box 349). For example, the patient may be presented with a webpage 380 as shown in FIG. 28a, with a window 381 containing the details 382 of the appointment and a button 383 to click to book the appointment. The patient may provide additional details about the patient's condition in the window 384 provided.

Figure 16:
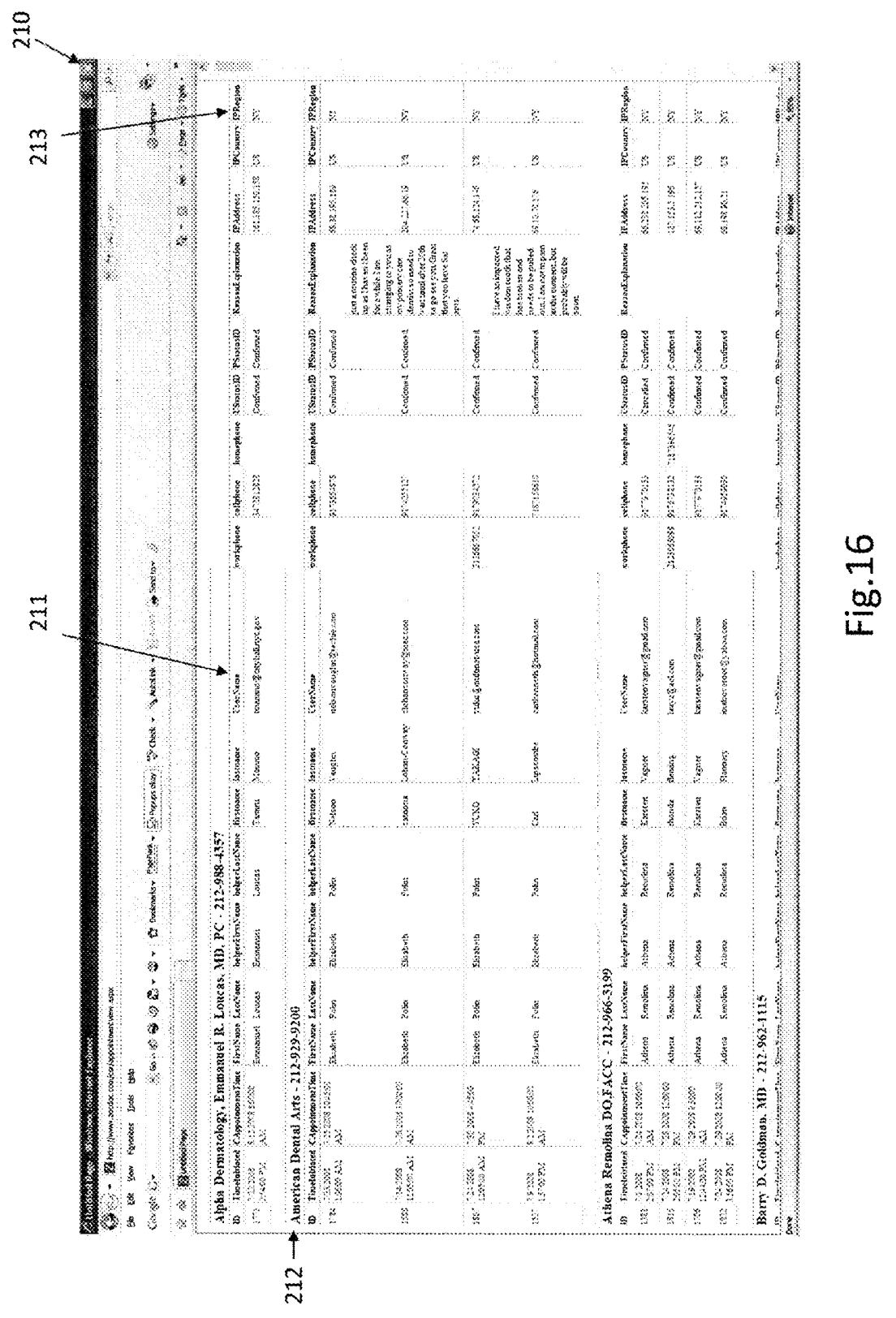

Returning to FIG. 25, upon receiving the patient's confirmation, the aggregator generates and sends an email 385 to the patient (Box 350) notifying the patient regarding the details of the appointment, as shown in FIG. 28b. The aggregator also sends an email notice 400 to the practitioner group (Box 351), such as that shown in FIG. 30, asking the practitioner to confirm the appointment. When the client confirms the appointment (Box 354), the patient is then sent a confirming email (Box 355), such as the email 390 shown in FIG. 29. The aggregator may also send the patient one or more reminders, such as one week prior, one day prior, and one hour prior to the appointment (Box 356). The aggregator's CSR tool is automatically updated with the confirmed appointment information (Box 357). This process is illustrated in FIG. 16.

As previously described, the client may be notified of a newly booked appointment, and of the client's need to confirm the booked appointment, in various ways. In one embodiment the client is notified on its computer via an alerter popup window with a message asking the client to confirm the newly booked appointment, as described previously with respect to FIG. 14. In another embodiment, the client is sent an email 400, such as shown in FIG. 30, asking the client to confirm within a defined time period the newly booked appointment. The email notification to the client includes the details of the booked appointment 401 and may include a link 402 for a response (or the client may reply by email). In both cases, following receipt of confirmation from the client, the aggregator updates the aggregator's database and the CSR tool for viewing confirmed appointments (as shown in FIG. 16).

Figure 31:
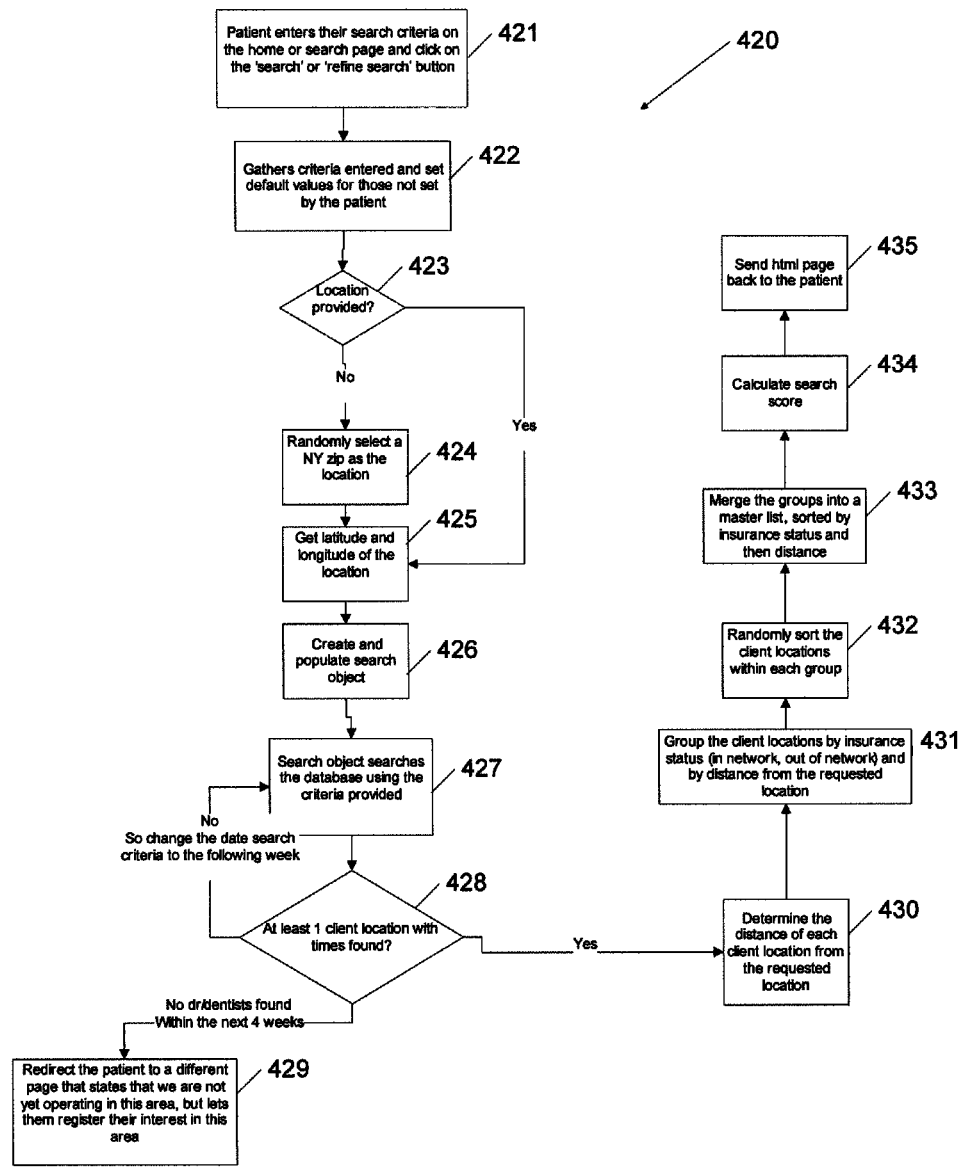
FIG. 31 is a flow diagram illustrating the operation and sequence of an embodiment of a software product of the present invention, for conducting a patient search of the aggregator database.

FIG. 31 is a flow diagram illustrating the operation and sequence of an embodiment of the software product of the present invention, for conducting a patient search of the aggregator database. The search algorithm queries the aggregator's database for client locations that match the patient's search criteria and then groups and sorts these locations and their associated practitioners and available appointment times to present the most useful results to the patient. The client locations are queried so that clients with multiple locations will appear more than once if they have several locations which match the search criteria. A search score is calculated and recorded at the end of the process which allows the aggregator to analyze the search process to ensure that patients are being presented with the best results.

The search criteria is entered by the patient on the aggregator's home page or search page and this data is sent to the aggregator as query parameters. If any criteria has not been specified by the patient, the process will provide a default value. Once the search process has determined the most appropriate clients and has sorted them, it will display them in the search page, transmitted to the patient's web browser in HTML format.

Referring to FIG. 31, according to the process 420 the patient enters the search criteria on the home or search page of the aggregator and clicks on the search or refine search button (Box 421). The process initially gathers the user's entered criteria and sets up the default values for any criteria not specified by the patient (Box 422). If the user has not entered the location in the criteria, the process will randomly select a zip code within the relevant area to insure that various areas are represented in a default location search (Box 424). The process then retrieves the latitude and longitude of the patient location based on the patient's IP address (Box 425), and creates a search object and populates it with the search criteria (Box 426). The search object then performs a search by querying the database for all client locations that offer the selected practitioner specialty in the region defined by the search location (Box 427). It is imperative that if the search does not return any clients, the process searches for appointments in the following week (returns to Box 427). If it does not find any clients it will repeat this step again up to a maximum of four times. If it does not find any clients after repeating this search four times, it will redirect the patient to the aggregator's webpage informing the patient that the aggregator's service is not yet available in the patient's designated area and prompting patients to register their interest in using the aggregator's service (when available) in their area (Box 429).

If the search returns at least one client location with available times meeting the search criteria (Box 428), the process will determine the distance from each client location to the patient location (Box 430) and organize them into groups based on this distance and the insurance status (in network, out of network) (Box431). The process then randomly sorts the clients in each group so that different clients appear toward the top of the list within their groups (Box 432). This ensures that clients are fairly represented in the aggregator's search. The groups are then merged into a master list which is sorted by insurance status and then distance (Box 433).

Finally, the process calculates a search score which allows the aggregator to verify the usefulness of the search results. The HTML formatted data is then returned to the patient and rendered in the patient's browser (Box 435).

As previously described, the available appointment times are filtered to insure that appointments can only be booked for times that allow the client sufficient time to confirm the appointment. For example, if an appointment is booked after 5:00 p.m. on a week day, the appointment cannot be booked before 11:00 a.m. on the following week day.

Figure 32:
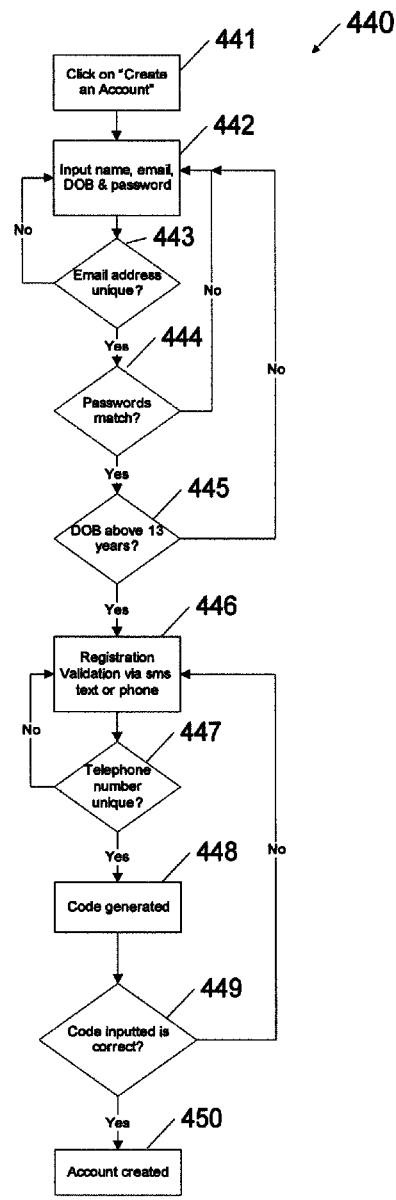
FIG. 32 is a flow diagram illustrating the operation and sequence of an embodiment of a software product of the present invention, for creating a patient account.

FIG. 32 is a flow diagram illustrating the operation and sequence of an embodiment of the software product of the present invention, for creating a patient account. In order for a patient account to be created with the aggregator, the patient must fulfill certain criteria, e.g., the following criteria:
- age above 13 years;
- email address has not been used for a previous account;
- telephone number has not been used for a previous account.

Further, to check the potential patient authenticity, a code is sent by the aggregator to the patient via a call or SMS message to the patient's phone. This code must then be entered by the patient on the aggregator's website to complete the account creation process. This prevents people from creating random email addresses and making fake appointments. It also insures that the aggregator has the correct phone number for the patient, which number can also be provided to the client.

Figure 33:
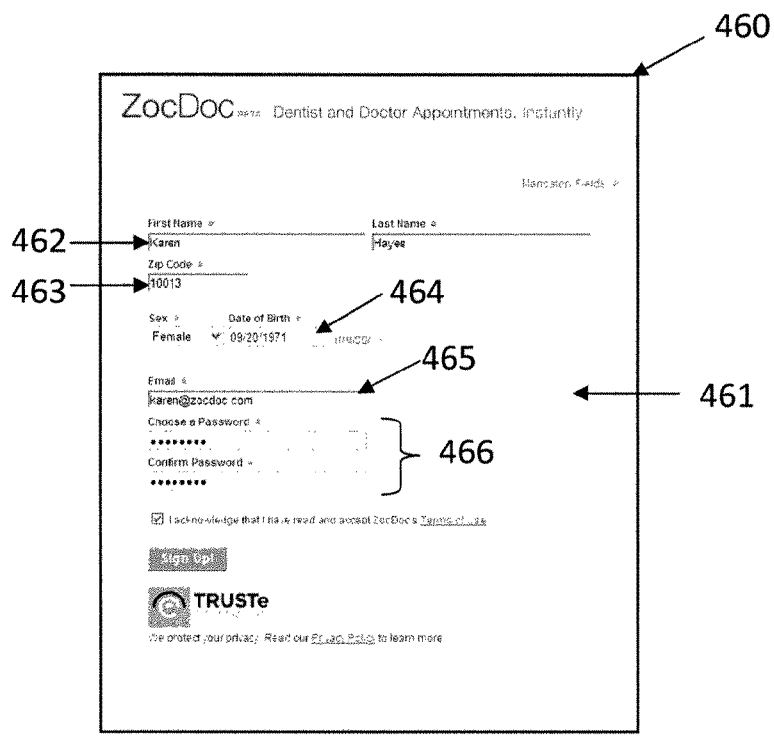
FIG. 33 is an exemplary webpage enabling a patient to create an account.
Figure 34:
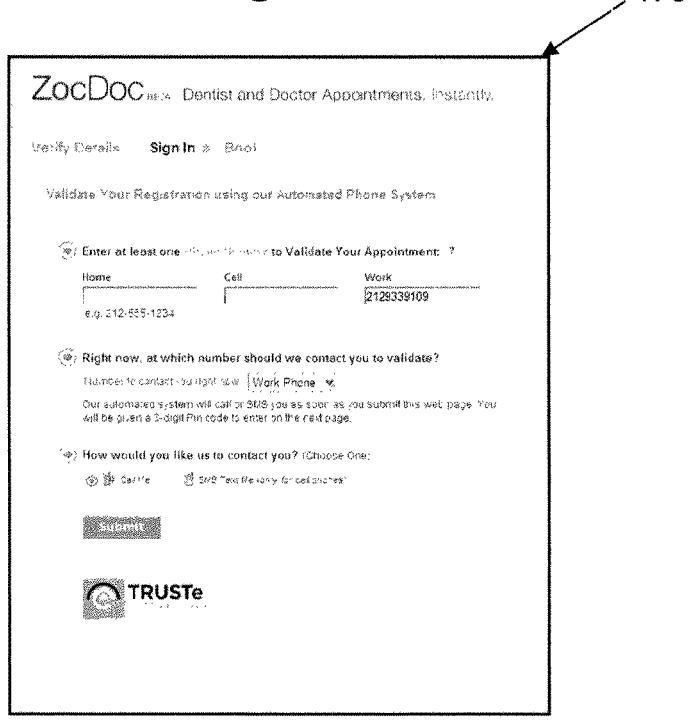
FIG. 34 is an exemplary webpage requesting a phone number from the patient to validate an appointment.
Figure 35:
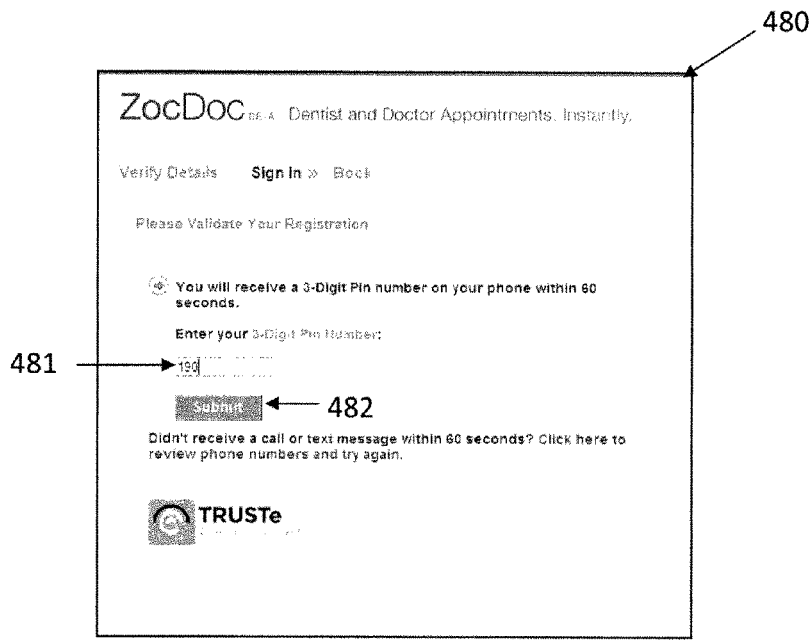
FIG. 35 is an exemplary webpage enabling a patient to enter a verification code.
Figure 36:
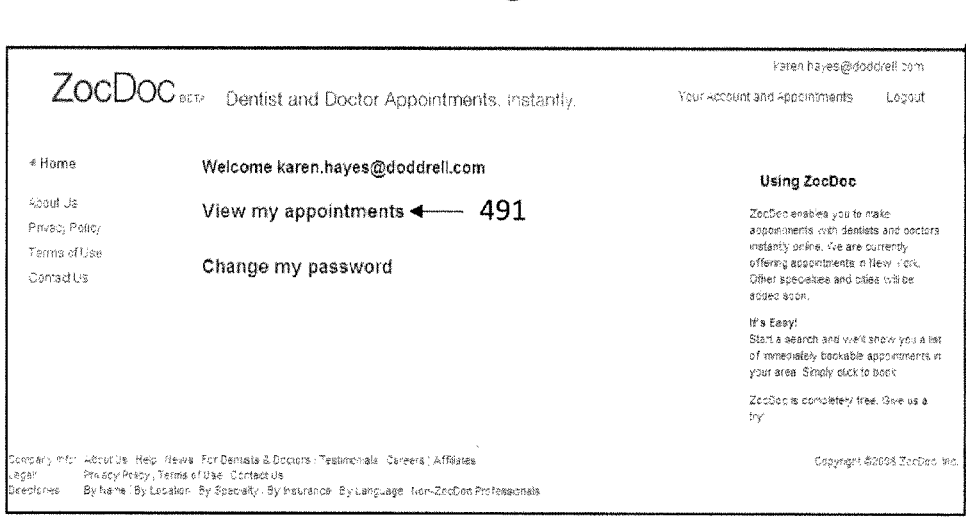
FIG. 36 is an exemplary webpage notifying a patient the account has been created.

Referring to the process 440 of FIG. 32, to create an account the patient clicks (Box 441) on a create-an-account button on the aggregator's webpage. The patient is then presented with a webpage 460 such as that shown in FIG. 33, with a window 461 asking the patient to input his name 462, location (zip code) 463, email address 465, date of birth 464, and choosing and confirming a password 466 (Box 442). The process checks to confirm the email address entered is unique (Box 443). If not, an error message is sent and the patient is sent back to the prior webpage 462 with an error message (Box 442). The process then determines whether the passwords entered in the two fields, chose a password and confirm the password, match (Box 444). If they do not, the patient is sent an error message and returned to the webpage of FIG. 33 (Box 442). If they match, the process checks if the patient's date of birth is above 13 years (Diamond 445). If not, the patient is returned with an error message to the webpage of FIG. 33 (Box 442). If the age requirement is met, the process initiates a registration validation process (Box 446). The patient is sent to a webpage 470 as shown in FIG. 34 requesting a phone number to validate the appointment, at which number the patient can now be reached, and a request whether to contact the patient via a live (or automated) call or text message (e.g., SMS text message for cell phones) (Box 446). The process then verifies whether the telephone number provided for immediate contact is unique in the aggregator database of patient accounts (Diamond 447). If not, an error message is returned to the patient to fix the items in the webpage of FIG. 34 (Box 446). If the telephone number is unique, the process generates a code (Box 448). The code is transmitted to the patient and the process awaits receipt of the code (entered by the patient on the aggregator's webpage) to determine whether it matches (Diamond 449). FIG. 35 illustrates an aggregator's webpage 480 wherein the patient is prompted to enter the code 481 and then hit submit 482 in order to validate the registration. If the inputted code is correct, the process allows the account to be created (Box 450). The patient is presented a webpage 490 notifying them that the account is created and inviting the patient via link 491 to view his appointments (FIG. 36).

Figure 37:
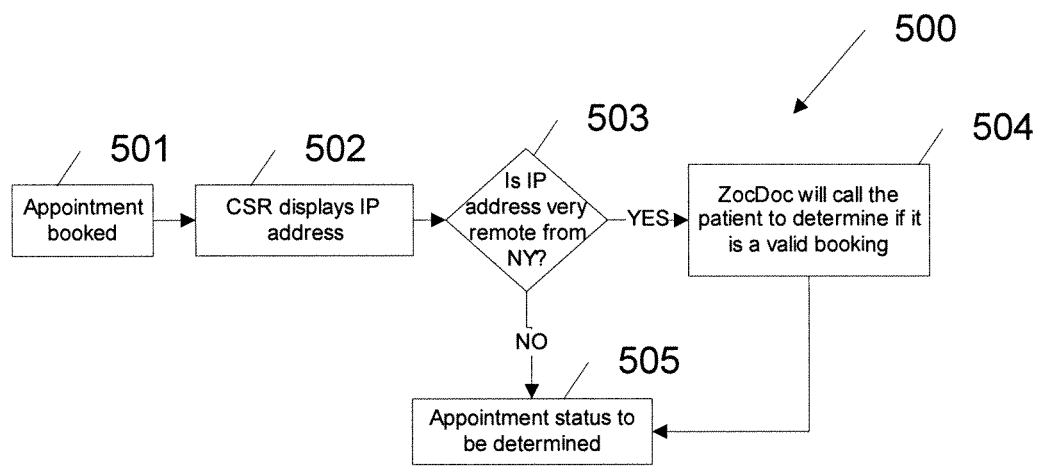
FIG. 37 is a flow diagram illustrating the operation and sequence of an embodiment of a software product of the present invention, for location verification.

FIG. 37 is a flow diagram illustrating the operation and sequence of an embodiment of the software product of the present invention, for verifying the patient location. This process helps detect and guard against bogus appointments.

With reference to the process 500 of FIG. 37, once an appointment is booked (Box 501) the process provides a display for an administrator of the aggregator, showing the IP address of the computer from which the patient booked the appointment, and its geographic location (Box 502). An example of such a display is shown in FIG. 16. If it is determined that the patient IP address is sufficiently remote from the search location criteria entered by the patient (Diamond 503), then the aggregator will call the patient by phone to determine whether this is a credible (valid) booking (Box 504). If the aggregator is satisfied that the appointment is valid, the appointment status will be confirmed in the aggregator database (Box 505). If the geographic location of the patient's IP address is sufficiently close to the search location criteria, then the appointment status can be confirmed without further validation. Also, when appointments are booked, the patient IP address can be used to calculate and then record the patient's country and region which are then logged with the request in the database.

Figure 38:
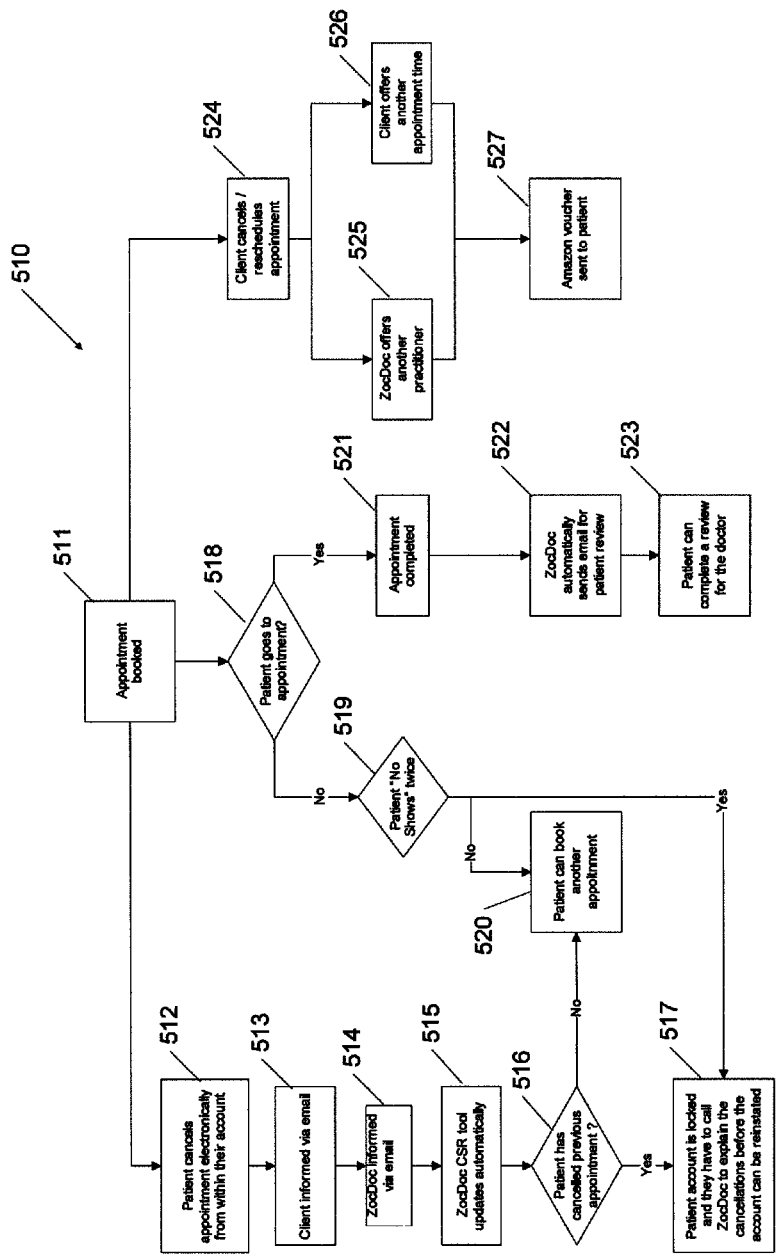
FIG. 38 is a flow diagram illustrating the operation and sequence of an embodiment of a software product of the present invention, for post appointment processing and gathering of patient feedback.

FIG. 38 is a flow diagram illustrating the operation and sequence of an embodiment of the software product of the present invention, providing more detail on a post appointment process which includes the gathering of patient feedback. To insure that all feedback is based on an actual patient visit, the aggregator insures that all patients that leave feedback have actually seen the respective client by confirming their appointment history. Only patients who have seen a client can leave feedback.

Figures 39, 40:
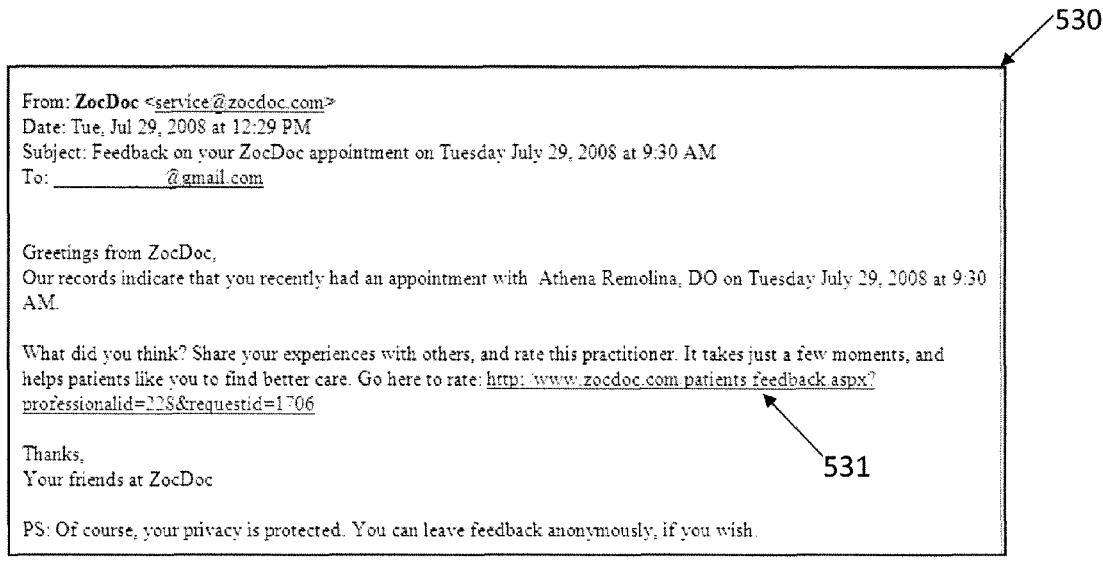
FIG. 39 is an exemplary email sent to a patient with a request to provide feedback.
FIG. 40 is an exemplary webpage enabling a client to enter patient feedback.

Referring to the process 510 of FIG. 38, once an appointment is booked (Box 511), it is determined whether the patient went to the appointment (Diamond 518), and whether the appointment was completed (Box 521); if so, then the aggregator automatically sends the patient an email soliciting patient review (Box 522). FIG. 39 is an example of such an email 530 sent to the patient, providing a link 531 for the patient to access a webpage wherein the patient can provide comments and responses to standardized ratings. Patients can then complete a review of the doctor by entering responses to the designated rating criteria and providing additional text comments before submitting the review (Box 523). FIG. 40 is an illustration of an aggregator's webpage 540 inviting patient feedback. It includes three specific rating categories, each including a number of alternative ratings, here a general recommendation 541, a rating on the practitioner's bedside manner 542, and rating on the amount of waiting time in the office before the patient was seen 543. The patient is provided with a window 544 for entering any additional text comments. The patient is given the option 545 to include or exclude his name on the review. The patient then hits the submit review button 546 and the feedback is provided to the aggregator.

Returning to FIG. 38, the disclosed process also includes a process for determining whether the patient canceled the appointment, or was a no-show. If the patient canceled the appointment electronically from within their (aggregrator) account (Box 512), the aggregator informs the client via email (Box 513) and the aggregator updates the CSR tool and informs its CSR (customer service representative) via an email (Boxes 514 and 515). If it is determined that the patient has canceled previous appointments (Diamond 516), then the patient may be locked out of making future appointments; the patient will have to explain to the aggregator the basis for the cancellations before the account can be reinstated (Box 517). If the patient has not previously canceled, then the patient is allowed to book another appointment (Box 520). If the patient no-shows twice, then the patient account is locked (Box 519).

If it was the client who canceled or rescheduled the appointment (Box 524), then the aggregator offers the patient another practitioner (Box 525) or the client offers the patient another appointment time (Box 526). The aggregator sends the patient a gift voucher to compensate for the inconvenience (Box 527).

System, Method and Computer Program Product

As will be appreciated by one skilled in the art, the present invention may be embodied as a system, method or computer program product. Accordingly, unless specified to the contrary, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer-usable or computer-readable medium(s) may be utilized, unless specified to the contrary herein. The computer-usable or computer-readable medium may be, for example but not limited to, electronic, magnetic, optical, electromagnetic, infrared, or semiconductor. More specific examples (a non-exhaustive list) include: a portable computer diskette, a hard disk, a random access memory (RAM), a read-only memory (ROM), an erasable programmable read-only memory (EPROM or Flash memory), a portable compact disc read-only memory (CDROM), an optical storage device.

Computer program code for carrying out operations of the present invention may be written in any combination of one or more programming languages, including an object oriented programming language such as Java, Smalltalk, C++, C#, JavaScript/Ajax and similar programming languages. JavaScript, which relies on a runtime environment in a web browser, is commonly used for website development (e.g., writing functions that are embedded in or included from HTML pages). JavaScript can be used as a scripting language for implementing an Ajax-embedded webpage. Unless otherwise specified, the program code may execute entirely on a user's computer, partly on the user's (e.g., patient or client) computer, as a stand-alone software package, partly on a user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A website is a collection of web pages posted on one or more web servers, accessible via the Internet. A webpage is a document, typically written in [X]HTML, that is generally accessible via HTTP, a protocol that transfers information from a web server to a display in the user's web browser. The collection of publically accessible websites are referred to as the "World Wide Web".

Websites are written in, or dynamically converted to, HTML (hyper text mark-up language) and are accessed using a software interface known as the user agent. Web pages can be viewed or otherwise accessed from a range of computer-based and Internet-enabled devices of various types, including desktop computers, laptop computers, PDA's and cell phones. A website is posted on a computer system known as a web server, and it includes software that retrieves and delivers the pages in response to requests from the website users.

A dynamic website presents variable information that is tailored to particular users. It may accept the user's input and respond to a user's request. For example, the user can enter text into a data entry field or form or select highlighted (linked) options, which prompts the website to fulfill the request and return a unique result. The aggregator's website, accessible in various forms to both patients and practice groups, includes such dynamic functionality.

A link or hyperlink, is a reference or navigation component in a document to another section of the same document or to another document on a different domain. A web browser usually displays a link in some distinguishing way, e.g. in a different color, font or style. When the user activates the link (e.g. by clicking on it with the mouse) the browser will display the target of the link.

As used herein, database and central database are not meant to be limiting, and may reside in one or more locations and/or data repositories. The aggregator's database is referred to as a central database to distinguish it from the separate multiple databases of the unaffiliated practice groups from which the aggregator combines (aggregates) the available appointment times to be offered on the aggregator's website.

The aggregator can, by collecting and storing this available appointment data from a plurality of unaffiliated practice groups, provide a much larger database of available appointment times/specialties/procedures and can allow patients to book appointments directly with the aggregator, without requiring the patients to contact the practice group in any manner (by phone, email or practice group website).

The present invention is described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The flowchart and block diagrams illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

By way of example only, various described embodiments may be implemented on process based servers, such as any x86_64 processor based server, for example running a Windows Operating System, e.g. Windows Server 2003, Windows XPNista, including Microsoft's NET Framework (e.g. Net 2.0). The database programming may be implemented in the SQL programming language (e.g. MS SQL 2005 and TSQL).

Modifications can be made to the previously described embodiments of the present invention and without departing from the scope of the invention, the embodiments being illustrative and not restrictive.

The invention claimed is:

1. A method for online booking of healthcare office appointments comprising:
storing, on an aggregator server, for each of a plurality of healthcare practitioners from a plurality of unaffiliated practice groups, a procedure and corresponding procedure duration for each practitioner,
wherein each stored procedure is selected from predefined procedure types and the procedure duration is individual to each associated practitioner;
maintaining, by the server, an aggregator database of updated available office appointment data individual to each practitioner, wherein maintaining comprises:
receiving, by the server, from a webpage for entry by the practice groups, available office appointment times for an associated practitioner in time blocks, wherein a time block includes multiple contiguous available appointment times for a particular practitioner and practitioner office location;
storing, by the server, in the aggregator database, the received time blocks as open time blocks for the associated practitioner;
pulling, by the server, from a synchronizer at the practice group of the associated practitioner, at least one booked appointment time; and
updating, by the server, the available appointment times in the aggregator database by modifying the open time blocks to remove the at least one booked appointment time pulled from the synchronizer;
receiving, by the server, from an associated website, a patient request identifying a procedure selected from one of the predefined procedure types;
processing, by the server, the patient request, for each practitioner having the identified procedure stored in the database, wherein processing comprises:
splitting the open time blocks of the practitioner based on the stored procedure duration of the practitioner to generate a plurality of individual start times; and
displaying, on the website, the plurality of individual start times for selection by the patient to book an office appointment on the website;
receiving, on the server, a patient selected start time; and
booking an office appointment at the selected start time with the associated practitioner and identified procedure, wherein booking comprises:
confirming, via the server, the booked appointment by notifying the patient; and
updating the available office appointment data stored in the aggregator database by modifying the stored open time blocks for the respective practitioner to remove the booked appointment time.

2. The method of claim 1, including:
creating an account, via the server, for the practice group prior to storing the available appointment times.

3. The method of claim 2, including:
the creating an account step includes registering individual practitioners in the practice group.

4. The method of claim 2, including:
the creating an account step includes storing in the aggregator database a profile for each individual practitioner in the practice group.

5. The method of claim 2, including:
the creating an account step includes storing in the aggregator database insurance plan information for individual practitioners in the practice group.

6. The method of claim 1, including:
receiving, by the server, from the website, a patient phone number; and
wherein the booking step further comprises verifying the phone number prior to booking the appointment.

7. The method of claim 6, wherein:
the verifying step includes contacting the patient via the phone number prior to booking the appointment for the patient.

8. The method of claim 1, including:
sending via the server, an electronic communication to the practice group of the respective practitioner with a request for confirmation of the booked appointment within a defined time.

9. The method of claim 8, including:
receiving via the server, an electronic communication with confirmation from the practice group; and
sending via the server, an electronic communication with a confirmation of the booked appointment time to the patient.

10. The method of claim 1, including:
storing in the aggregator database one or more predefined practitioner specialties for each practitioner;
receiving with the patient request data identifying a predefined practitioner specialty for a search of the aggregator database; and
wherein the processing step is limited to each practitioner having stored on the database the identified procedure and identified specialty.

11. The method of claim 1 or 10, including:
storing on the aggregator database one or more locations for each practitioner; and
receiving with the patient request data identifying a location for a search of the aggregator database; and
wherein the processing step is limited to each practitioner having stored on the database the identified procedure and a location within the identified location .

12. The method of claim 1, including:
storing on the aggregator database one or more insurance categories for each practitioner; and
receiving with the patient request data identifying an insurance category for a search of the aggregator database; and
wherein the processing step is limited to each practitioner having stored on the database the identified procedure and identified insurance category.

13. The method of claim 1, including:
storing on the aggregator database practitioner profile information; and
receiving with the patient request data identifying practitioner profile information for a search of the aggregator database; and
wherein the processing step is limited to each practitioner having stored on the database the identified procedure and profile information within the identified profile information.

14. The method of claim 1, including:
receiving with the patient request data identifying a desired appointment date for a search of the aggregator database; and
wherein the processing step is limited to each practitioner having stored in the database available appointment time on the identified date.

15. The method of claim 1, wherein:
the maintaining step includes maintaining records of booking information on the aggregator database for each of the booked appointments.

16. A computer network based scheduling system for healthcare office appointments comprising:
an aggregator database configured to store available office appointment times for a plurality of healthcare practitioners from a plurality of unaffiliated practice groups, and a procedure and corresponding procedure duration for each practitioner,
wherein each stored procedure is selected from predefined procedure types and the procedure duration is individual to each associated practitioner;
a computer, communicating on a computer network with the aggregator database, configured to receive, from a webpage for entry by the practice groups, available office appointment times for an associated practitioner in time blocks, wherein a time block includes multiple contiguous available appointment times for a particular practitioner and practitioner office location, store on the aggregator database the received time blocks as open time blocks for the associated practitioner, pull at least one booked appointment time from a synchronizer at the practice group of the associated practitioner, and update the available appointment times in the aggregator database by modifying the open time blocks to remove the at least one booked appointment time pulled from the synchronizer, wherein the computer is further configured to operate via the computer network to:
receive, from an associated website, a patient request identifying a procedure selected from one of the predefined procedure types;
process the patient request for each practitioner having the identified procedure stored in the database, wherein processing comprises:
splitting the open time blocks of the practitioner based on the stored procedure duration of the practitioner to generate a plurality of individual start times; and
displaying, on the website, the plurality of individual start times for selection by the patient to book an office appointment on the website;
receive from the website a patient selected start time; and
book an office appointment at the selected start time with the associated practitioner and identified procedure, wherein booking comprises:
confirming the booked appointment by notifying the patient; and
updating the available office appointment data stored in the aggregator database by modifying the stored open time blocks for the respective practitioner to remove the booked appointment time.

17. The system of claim 16, including:
the aggregator database further configured to store one or more predefined practitioner specialties for each practitioner;
the computer further configured to receive with the patient request data identifying a predefined practitioner specialty for a search of the aggregator database; and
wherein the processing steps are limited to each practitioner having stored on the database the identified procedure and identified practitioner specialty.

18. The system of claim 16, including:
the aggregator database further configured to store one or more locations for each practitioner;
the computer further configured to receive with the patient request data identifying a location for a search of the aggregator database; and
wherein the processing steps are limited to each practitioner having stored on the database the identified procedure and a location within the identified location.

19. The system of claim 16, including:
the aggregator database further configured to store one or more insurance categories for each practitioner;
the computer further configured to receive with the patient request data identifying an insurance category for a search of the aggregator database; and
wherein the processing steps are limited to each practitioner having stored on the database the identified procedure and identified insurance category.

* * * * *